US011534076B2

(12) United States Patent
Nebuya et al.

(10) Patent No.: US 11,534,076 B2
(45) Date of Patent: Dec. 27, 2022

(54) IMAGE GENERATION APPARATUS, CONDUCTIVITY ACQUISITION APPARATUS, IMAGE GENERATION METHOD, AND PROGRAM

(71) Applicant: SCHOOL JURIDICAL PERSON KITASATO INSTITUTE, Tokyo (JP)

(72) Inventors: Satoru Nebuya, Sagamihara (JP); Hiroshi Kumagai, Sagamihara (JP); Hideyuki Suzuki, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 633 days.

(21) Appl. No.: 15/121,116

(22) PCT Filed: Feb. 25, 2015

(86) PCT No.: PCT/JP2015/055433
§ 371 (c)(1),
(2) Date: Dec. 5, 2016

(87) PCT Pub. No.: WO2015/129756
PCT Pub. Date: Sep. 3, 2015

(65) Prior Publication Data
US 2017/0071499 A1    Mar. 16, 2017

(30) Foreign Application Priority Data

Feb. 25, 2014  (JP) .............................. JP2014-034335

(51) Int. Cl.
*A61B 5/0536* (2021.01)
*A61B 5/05* (2021.01)
(Continued)

(52) U.S. Cl.
CPC .......... *A61B 5/0536* (2013.01); *A61B 5/0033* (2013.01); *A61B 5/05* (2013.01);
(Continued)

(58) Field of Classification Search
CPC ....... A61B 5/0536; A61B 5/062; A61B 5/063; A61B 5/05; A61B 5/068; A61B 5/0033;
(Continued)

(56) References Cited

U.S. PATENT DOCUMENTS 5,421,345 A * 6/1995 Lekholm .............. A61B 5/0535
600/506
6,501,984 B1 * 12/2002 Church ................ A61B 5/0536
600/547
(Continued)

FOREIGN PATENT DOCUMENTS

GB    2481506    12/2011
JP    6-225860    8/1994
(Continued)

OTHER PUBLICATIONS

Janczulewicz, A., & Wtorek, J. (2007). Properties of CMT studies by means of FEM and Spice model. In 13th International Conference on Electrical Bioimpedance and the 8th Conference on Electrical Impedance Tomography (pp. 52-55). Springer, Berlin, Heidelberg. (Year: 2007).*

(Continued)

*Primary Examiner* — Carolyn A Pehlke
*Assistant Examiner* — Johnathan Maynard
(74) *Attorney, Agent, or Firm* — Nixon & Vanderhye, P.C.

(57) ABSTRACT

An image generation apparatus includes a plurality of electrodes, a plurality of sensor cells, and a controller configured to provide a tomographic image of a measurement object on the basis of an intensity of a magnetic field generated by an alternating current supplied via the plurality of electrodes. The controller acquires the intensity of the magnetic field via the plurality of sensor cells.

22 Claims, 14 Drawing Sheets

(51) Int. Cl.
*A61B 5/06* (2006.01)
*A61B 5/00* (2006.01)
A61B 5/0522 (2021.01)

(52) U.S. Cl.
CPC .............. *A61B 5/062* (2013.01); *A61B 5/063* (2013.01); *A61B 5/068* (2013.01); *A61B 5/0522* (2013.01); *A61B 2562/0223* (2013.01); *A61B 2576/00* (2013.01)

(58) Field of Classification Search
CPC .......... A61B 2562/0223; A61B 5/0522; A61B 2576/00
See application file for complete search history.

(56) References Cited

U.S. PATENT DOCUMENTS

| | | | |
|---|---|---|---|
| 2003/0016010 A1 | 1/2003 | Kandori et al. | |
| 2005/0054911 A1* | 3/2005 | Nachman | A61B 5/0536 600/411 |
| 2005/0054939 A1* | 3/2005 | Ben-Ari | A61B 5/245 600/506 |
| 2006/0122523 A1* | 6/2006 | Bonmassar | A61B 5/053 600/506 |
| 2006/0125475 A1* | 6/2006 | Sodickson | A61B 5/0536 600/416 |
| 2007/0088210 A1* | 4/2007 | Woo | G01R 33/4808 600/410 |
| 2008/0004904 A1* | 1/2008 | Tran | A61B 5/411 340/286.07 |
| 2008/0258717 A1* | 10/2008 | Igney | A61B 5/0522 324/222 |
| 2009/0143665 A1 | 6/2009 | Seki et al. | |
| 2009/0243619 A1 | 10/2009 | Bespalov et al. | |
| 2009/0253976 A1 | 10/2009 | Harlev et al. | |
| 2010/0113910 A1 | 5/2010 | Brauers et al. | |
| 2011/0308859 A1* | 12/2011 | Bittar | E21B 47/022 175/45 |
| 2012/0043969 A1* | 2/2012 | Holder | A61B 5/0536 324/600 |
| 2013/0150702 A1* | 6/2013 | Hokari | A61B 5/243 600/409 |
| 2013/0197389 A1 | 8/2013 | Levin et al. | |
| 2013/0217993 A1* | 8/2013 | Brunner | A61B 5/0536 600/393 |
| 2014/0058212 A1 | 2/2014 | Wang | |
| 2015/0219481 A1* | 8/2015 | Kersey | G01F 1/584 73/861.08 |
| 2015/0219732 A1* | 8/2015 | Diamond | A61B 5/04008 324/201 |
| 2016/0091448 A1* | 3/2016 | Soleimani | G01N 27/22 324/654 |
| 2016/0143540 A1* | 5/2016 | Gencer | A61B 8/00 600/438 |

FOREIGN PATENT DOCUMENTS

| | | |
|---|---|---|
| JP | 2006-508734 | 3/2006 |
| JP | 2009-125396 | 6/2009 |
| JP | 2009-523037 | 6/2009 |
| JP | 2010-524620 | 7/2010 |
| JP | 2012-228514 | 11/2012 |
| JP | 2013-022310 | 2/2013 |
| JP | 2013-542782 | 11/2013 |
| WO | WO 2004/049942 | 6/2004 |
| WO | WO 2007/070997 | 6/2007 |
| WO | WO 2009/144461 | 12/2009 |

OTHER PUBLICATIONS

Janczulewicz, A., Bujnowski, A., & Wtorek, J. (2009). Electro-Magnetic impedance tomography—a sensitivity analysis. In 4th European Conference of the International Federation for Medical and Biological Engineering (pp. 732-735). Springer, Berlin, Heidelberg. (Year: 2009).*

Janczulewicz, A., Wtorek, J., & Bujnowski, A. (2009). An CMT reconstruction algorithm for detection of objects buried in a half-space. In 4th European Conference of the International Federation for Medical and Biological Engineering (pp. 1074-1077). Springer, Berlin, Heidelberg. (Year: 2009).*

Korjenevsky, A. V. (2004). Electric field tomography for contactless imaging of resistivity in biomedical applications. Physiological measurement, 25(1), 391. (Year: 2004).*

Korjenevsky, A. V. (2005). Maxwell-Wagner relaxation in electrical imaging. Physiological measurement, 26(2), S101. (Year: 2005).*

Korjenevsky, A. V., & Tuykin, T. S. (2007). Electric field tomography: setup for single-channel measurements. Physiological measurement, 28(7), S279. (Year: 2007).*

Korjenevsky, A. V., & Tuykin, T. S. (2008). Phase measurement for electric field tomography. Physiological measurement, 29(6), S151. (Year: 2008).*

Tozer, J. C., Ireland, R. H., Barber, D. C., & Barker, A. T. (1999). Magnetic Impedance Tomography a. Annals of the New York Academy of Sciences, 873(1), 353-359. (Year: 1999).*

Levy, S., Adam, D., & Bresler, Y. (2002). Electromagnetic impedance tomography (EMIT): a new method for impedance imaging. IEEE transactions on medical imaging, 21(6), 676-687. (Year: 2002).*

International Search Report issued in PCT/JP2015/055433 dated May 26, 2015.

Office Action issued in EP Appln. No. 15 754 467.7 dated Sep. 24, 2018.

European Search Report issued in Appln. No. 15754467.7 dated Oct. 9, 2017.

Office Action issued in JP Appln. No. 2019-153863 dated Sep. 1, 2020 (w/ translation).

Ahlfors et al., "Magnetic Imaging of Conductivity" 14th Annual International Conference of the IEEE Engineering in Medicine and Biology Society, 1992, DOI: 10. 1109/IEMBS. 1992, 5762007.

Search Report issued in EP App. No. 20181100.7 dated Dec. 4, 2020, 7 pages.

Office Action dated May 18, 2022 issued in European Application No. 20181100.7 (5 pages).

* cited by examiner

IMAGE GENERATION APPARATUS, CONDUCTIVITY ACQUISITION APPARATUS, IMAGE GENERATION METHOD, AND PROGRAM

This application is the U.S. national phase of International Application No. PCT/JP2015/055433 filed 25 Feb. 2015 which designated the U.S. and claims priority to JP Patent Application No. 2014-034335 filed 25 Feb. 2014, the entire contents of each of which are hereby incorporated by reference.

TECHNICAL FIELD

The present invention relates to an image generation apparatus, a conductivity acquisition apparatus, an image generation method, and a program for acquiring a tomographic image of an object.

Priority is claimed on Japanese Patent Application No. 2014-034335, filed Feb. 25, 2014, the content of which is incorporated herein by reference.

BACKGROUND

An electrical impedance tomography (hereinafter referred to as EIT) measurement apparatus is technology for causing a weak current to flow from a pair of electrodes attached on a body surface and generating an image of a conductivity distribution or a distribution of a conductivity change within a living body from a potential difference generated on the body surface.

Because it is possible to acquire a tomographic image when a weak current flows through an object, EIT measurement has advantages in that there is no exposure problem and in that size reduction, long-time measurement, and real-time measurement are facilitated as compared with X-ray computed tomography (CT).

In the EIT measurement, generally, about 8 to 64 electrodes are used. These electrodes are attached to the body surface of the periphery of an object portion and signal cables individually connected to the electrodes are routed and connected to a measurement circuit. Recently, a method of integrating a plurality of electrodes and signal cables as a module and facilitating attachment/detachment of the electrodes and setting of a measurement apparatus has been attempted (for example, see Patent Literatures 1 and 2).

RELATED ART DOCUMENTS

Patent Document

[Patent Document 1]
Japanese Patent Application, Publication No. 2012-228514
[Patent Document 2]
Japanese Patent Application, Publication No. 2009-523037

SUMMARY OF INVENTION

Technical Problem

However, in all the EIT measurements described above, an operation of attaching a plurality of electrodes on a body surface is required. Therefore, even when it is facilitated to a certain extent by modularization, a fixed burden is considerably imposed on a measurement operator. Also, a physical burden is strong according to a measurement object person (a person to be measured) at the time of attachment of the electrodes.

An objective of aspects of the present invention is to provide an image generation apparatus, a conductivity acquisition apparatus, an image generation method, and a program capable of more easily and precisely acquiring a state of an object.

Solution to Problem

An aspect of the present invention is an image generation apparatus including: a plurality of electrodes; a plurality of sensor cells; and a controller configured to provide a tomographic image of a measurement object on the basis of an intensity of a magnetic field generated by an alternating current supplied via the plurality of electrodes, wherein the intensity of the magnetic field is acquired via the plurality of sensor cells.

Furthermore, an aspect of the present invention is an image generation apparatus including: an alternating current input unit configured to input an alternating current to a measurement object via an electrode arranged at a position separated from the measurement object; a magnetic field information acquisition unit configured to acquire an intensity of a magnetic field generated on the basis of the alternating current input by the alternating current input unit via a magnetic sensor arranged at a position separated from the measurement object; and an image generation unit configured to generate a tomographic image of the measurement object on the basis of the intensity of the magnetic field acquired by the magnetic field information acquisition unit.

Also, in the above-described image generation apparatus of the present invention, the magnetic field information acquisition unit is configured to acquire at least intensities of magnetic fields at a plurality of positions surrounding a specific tomographic surface of the measurement object.

Also, in the above-described image generation apparatus of the present invention, the alternating current input unit is configured to input the alternating current via electrodes arranged at a plurality of positions surrounding a specific tomographic surface of the measurement object.

Also, in the above-described image generation apparatus of the present invention, the magnetic field information acquisition unit is configured to acquire an intensity of a magnetic field generated on the basis of an alternating current input by the alternating current input unit via the magnetic sensor arranged around the same tomographic surface as the specific tomographic surface.

Also, in the above-described image generation apparatus of the present invention, the magnetic field information acquisition unit is configured to acquire intensities of magnetic fields at a plurality of positions surrounding another tomographic surface different from one tomographic surface of the measurement object simultaneously with intensities of magnetic fields at a plurality of positions surrounding the one tomographic surface.

Also, in the above-described image generation apparatus of the present invention, the image generation unit is configured to generate a tomographic image in which the one tomographic surface is represented by combining a first intermediate image generated on the basis of the intensities of the magnetic fields surrounding the one tomographic surface and a second intermediate image generated on the basis of the intensities of the magnetic fields at the plurality of positions surrounding the other tomographic surface.

Also, in the above-described image generation apparatus of the present invention, the alternating current input unit has a non-magnetic material as the electrode.

Also, in the above-described image generation apparatus of the present invention, the magnetic field information acquisition unit has an optical pumping atomic magnetic sensor as the magnetic sensor.

Also, in the above-described image generation apparatus of the present invention, the alternating current input unit is configured to input at least the alternating current via electrodes arranged at a plurality of positions surrounding a periphery of a specific tomographic surface of the measurement object.

Furthermore, an aspect of the present invention is an image generation method including: inputting an alternating current to a measurement object via an electrode arranged at a position separated from the measurement object; acquiring an intensity of a magnetic field generated on the basis of the input alternating current via a magnetic sensor arranged at a position separated from the measurement object; and generating a tomographic image of the measurement object using the acquired intensity of the magnetic field.

Furthermore, an aspect of the present invention is a program for causing an image generation apparatus to function as: an alternating current input means configured to input an alternating current to a measurement object via an electrode arranged at a position separated from the measurement object; a magnetic field information acquisition means configured to acquire an intensity of a magnetic field generated on the basis of the alternating current input by the alternating current input means via a magnetic sensor arranged at a position separated from the measurement object; and an image generation means configured to generate a tomographic image of the measurement object on the basis of the intensity of the magnetic field acquired by the magnetic field information acquisition means.

Furthermore, an aspect of the present invention is a conductivity acquisition apparatus including: an alternating current input unit configured to input an alternating current to a measurement object via an electrode arranged at a position separated from the measurement object; a magnetic field information acquisition unit configured to acquire an intensity of a magnetic field generated on the basis of the alternating current input by the alternating current input unit via a magnetic sensor arranged at a position separated from the measurement object; and a conductivity acquisition unit configured to acquire conductivity of the measurement object around which the magnetic sensor is arranged on the basis of the intensity of the magnetic field acquired by the magnetic field information acquisition unit.

Advantageous Effects of Invention

It is possible to more easily and precisely acquire a state of an object according to the above-described image generation apparatus, conductivity acquisition apparatus, image generation method, and program.

DESCRIPTION OF EMBODIMENTS

First Embodiment

[Overall Configuration]

Hereinafter, an image generation apparatus according to the first embodiment will be described with reference to the drawings.

Figure 1:
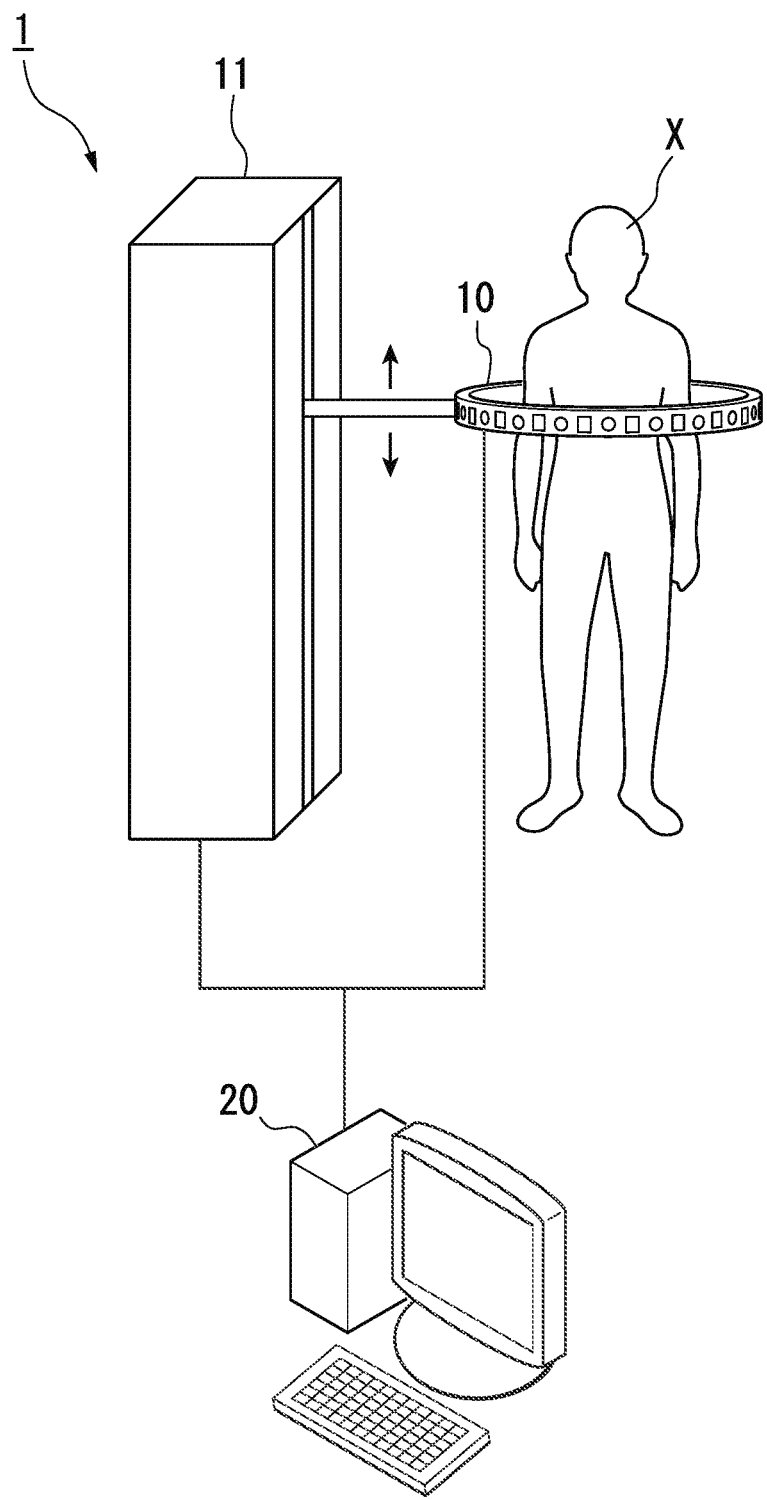
FIG. 1 is a diagram illustrating an overview of an image generation apparatus according to a first embodiment.

FIG. 1 is a diagram illustrating an overview of the image generation apparatus according to the first embodiment.

The image generation apparatus 1 illustrated in FIG. 1 includes a detection unit 10, a drive unit 11, and a main body unit (a controller) 20, and can acquire a tomographic image of a measurement object person (a person to be measured) X.

The detection unit 10 is formed in an annular shape to surround the girth of the measurement object person X at the time of use. Here, the "annular shape" is an overall shape surrounding at least a part of the object and is not limited to a shape which fully continuously surrounds the object. Also, the "annular shape" is not limited to a circle and may be various forms. For example, the "annular shape" can include an annular shape having a partial open section, a ring having an overall shape other than the circle, etc. As will be described below, the detection unit 10 has a plurality of electrodes and sensors (a plurality of magnetic sensors, a plurality of sensors, a plurality of sensor cells, and a plurality of sensor heads). The main body unit 20 acquires various types of detection signals for the measurement object person X from the detection unit 10. The main body unit 20 can acquire a tomographic image of a surface in which the detection unit 10 is arranged in the measurement object person X (a tomographic image of the person X to be measured with respect to a surface set according to a position of an axial direction of the detection unit 10) on the basis of the detection signal.

The drive unit 11 has a movement body which is fixed to the detection unit 10 and moves the detection unit 10 along a surface of the object (e.g., an axial direction and an up/down direction (a vertical direction) of the object (a portion to be measured)). In an example, according to linear movement of the movement body, the detection unit 10 can linearly move. Also, the movement of the detection unit 10 by the drive unit 11 is not limited to linear movement. The drive unit 11 has a drive mechanism such as, for example, a stepping motor (not illustrated). The drive unit 11 changes a position of the detection unit 10 (e.g., a position in the vertical direction) on the basis of an electrical signal (an instruction signal) input from the main body unit 20. Thereby, the operator can arbitrarily change a relative position of the detection unit 10 with respect to the measurement object person X. It is possible to easily acquire a desired tomographic image of the measurement object person X by moving the detection unit 10 using the drive unit 11. In an alternative embodiment, the image generation apparatus 1 can have a configuration in which the detection unit 10 is moved without using power or in which the drive unit 11 is substantially omitted.

The main body unit (the controller) 20 performs overall control of the image generation process of the image generation apparatus 1 such as the acquisition of the detection signal by the detection unit 10, the driving of the detection unit 10 using the drive unit 11, and the generation of a tomographic image. A detailed functional configuration of the main body unit 20 will be described below.

[Functional Configuration of Main Body Unit]

Figure 2:
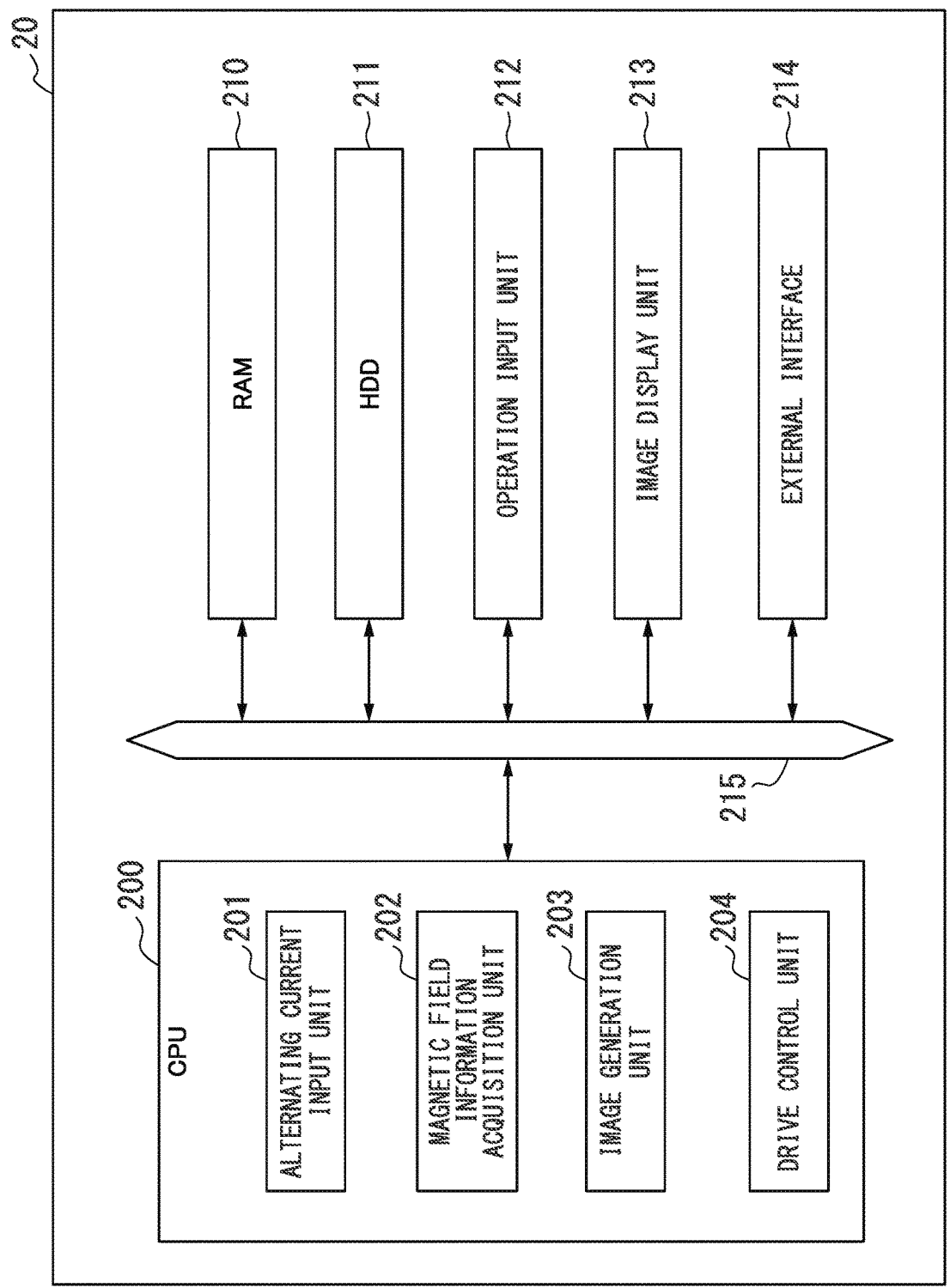
FIG. 2 is a diagram illustrating a functional configuration of a main body unit according to the first embodiment.

FIG. 2 is a diagram illustrating a functional configuration of the main body unit according to the first embodiment.

As illustrated in FIG. 2, the main body unit 20 according to the present embodiment includes a central processing unit (CPU) 200, a random access memory (RAM) 210, a hard disk drive (HDD) 211, an operation input unit 212, an image display unit 213, and an external interface 214.

The CPU 200 controls the overall image generation process of the image generation apparatus 1. The CPU 200 exhibits functions serving as an alternating current input unit 201, a magnetic field information acquisition unit 202, and an image generation unit 203 by performing an operation on the basis of a measurement program loaded to a predetermined storage region (the RAM 210 or the like).

The RAM 210 is a storage region serving as a work area of the CPU 200 which operates on the basis of the measurement program.

The HDD 211 is a storage means which stores various types of programs or a tomographic image or the like generated by the image generation unit 203.

The operation input unit 212 is constituted of, for example, a mouse, a keyboard, a touch panel, etc., and receives inputs of various operations by the operator.

The image display unit 213 is a liquid crystal display or the like and displays information necessary for an operation of the operator, an acquired tomographic image, or the like.

The external interface 214 is a communication interface for communicating with an external device and is particularly connected to the detection unit 10 and the drive unit 11 via a dedicated communication cable in the present embodiment.

Also, as illustrated in FIG. 2, the CPU 200, the RAM 210, the HDD 211, the operation input unit 212, the image display unit 213, and the external interface 214 are mutually connected via a system bus 215.

[Specific Function of CPU]

Next, the alternating current input unit 201, the magnetic field information acquisition unit 202, the image generation unit 203, and the drive control unit 204 implemented by an operation of the CPU 200 based on the measurement program will be briefly described.

The alternating current input unit 201 inputs an alternating current to the measurement object person X via a plurality of electrodes 102 (illustrated in FIG. 3) arranged at positions separated from the measurement object (the measurement object person X).

The magnetic field information acquisition unit 202 acquires a magnetic field generated on the basis of the alternating current input by the alternating current input unit 201 via a plurality of magnetic sensors (a plurality of sensor cells and a plurality of sensor heads) 103 arranged at positions separated from the measurement object person X.

The image generation unit 203 generates a tomographic image of the measurement object person X on the basis of the magnetic field acquired by the magnetic field information acquisition unit 202.

The drive control unit 204 outputs a predetermined drive instruction signal to the drive unit 11 and controls the operation of the drive unit 11.

More specific functions of the alternating current input unit 201, the magnetic field information acquisition unit 202, the image generation unit 203, and the drive control unit 204 will be described below.

[Structure of Detection Unit]

Figure 3:
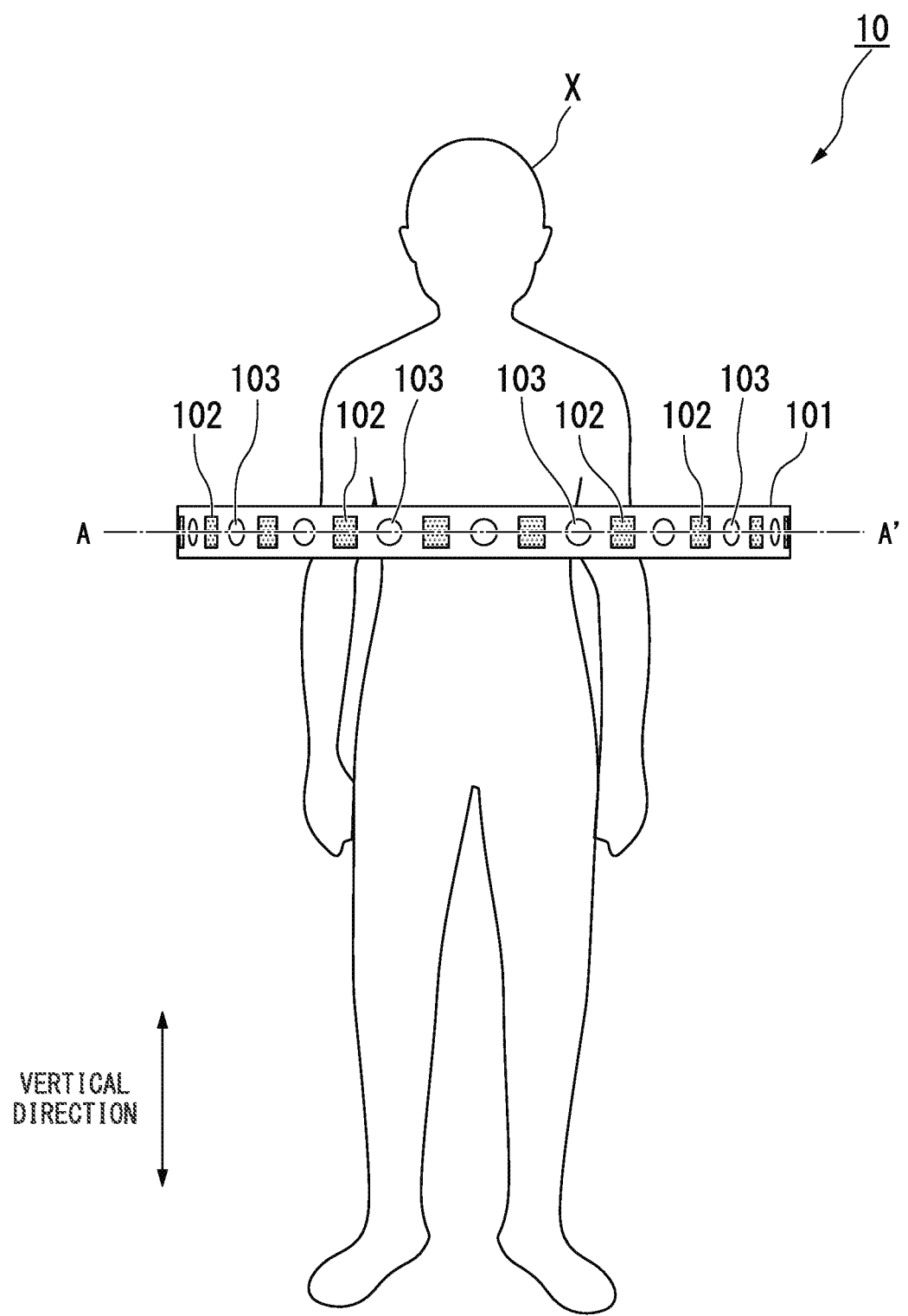
FIG. 3 is a first diagram illustrating a structure of a detection unit according to the first embodiment.
Figure 4:
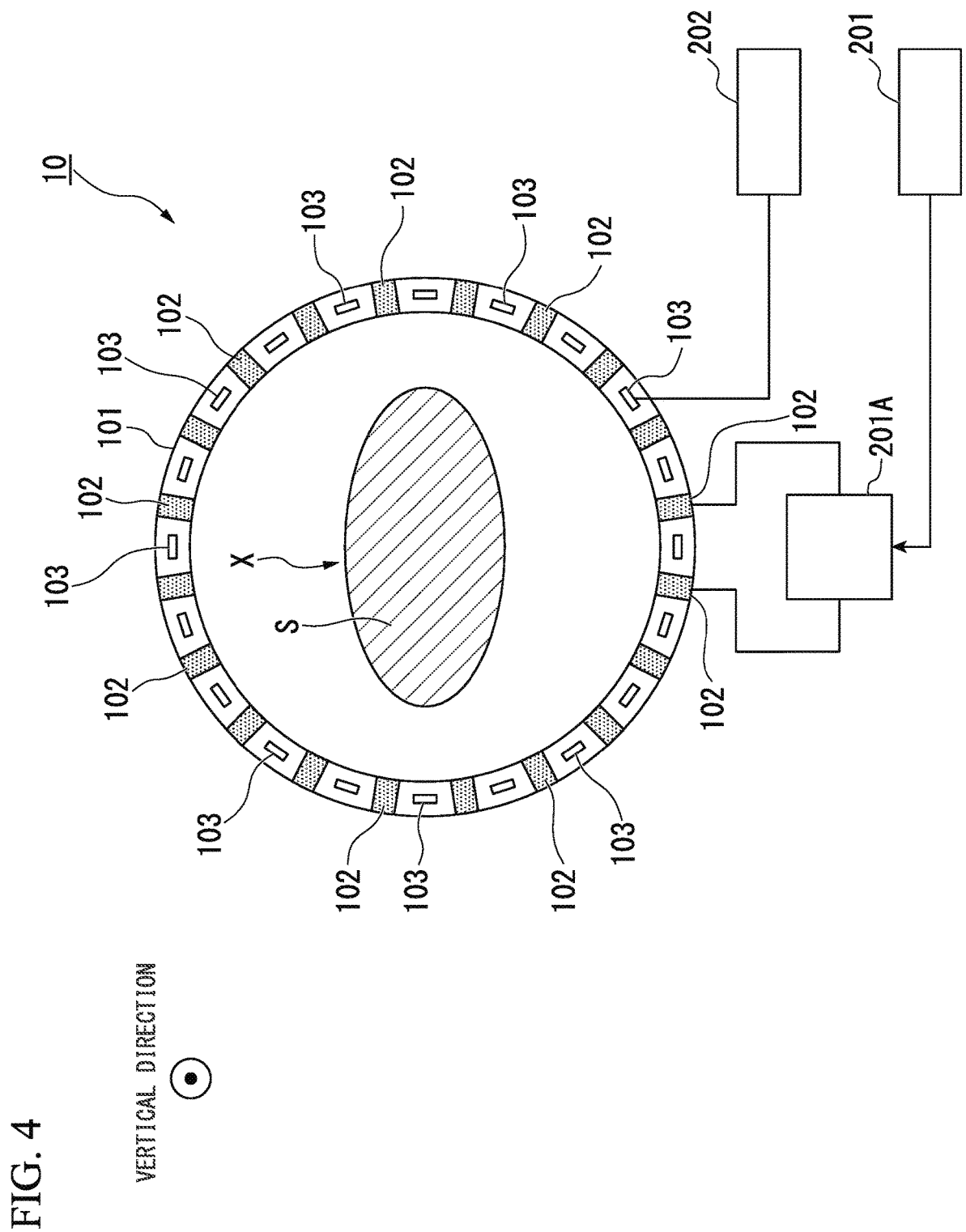
FIG. 4 is a second diagram illustrating the structure of the detection unit according to the first embodiment.

FIG. 3 is a first diagram illustrating the structure of the detection unit according to the first embodiment. Also, FIG. 4 is a second diagram illustrating the structure of the detection unit according to the first embodiment.

In FIG. 3, a structure of a side surface of the detection unit 10 is illustrated. Also, in FIG. 4, a cross-sectional structure of the surface A-A' in FIG. 3 is schematically illustrated. As illustrated in FIGS. 3 and 4, the detection unit 10 includes a base member (a base frame and an annular housing) 101, electrodes 102, and magnetic sensors 103.

In the present embodiment, the base member 101 is formed in an annular shape to surround the girth of the measurement object person X (to surround at least a part of the measurement object person) at the time of use. The base member 101 is attached to the drive unit 11 (FIG. 1). A relative position of the base member 101 with respect to the measurement object person X is changed on the basis of drive control by the drive unit 11. The base member 101 is formed of, for example, an acrylic resin or the like. Various materials can be applied as a material of the base member 101. Preferably, the material of the base member is substantially an insulator and is substantially a non-magnetic material. Also, the base member 101 is not limited to a circular annular shape. The overall shape of the base member 101 may be, for example, an oval shape or a partially intermittent structure. Alternatively, the base member 101 may have a structure in which the overall shape is changeable or a structure capable of being opened/closed. A plurality of electrodes 102 are attached to the base member 101 at fixed intervals in a circumferential direction of the base member 101 within the same surface as the surface A-A'. The arrangement of the electrodes 102 can be variously changed. The electrode 102 has, for example, conductivity of copper, aluminum, stainless steel, or the like and is formed of substantially a non-magnetic material. The material of the electrode 102 is not limited to the above-described examples.

Similar to the electrodes 102, a plurality of magnetic sensors 103 (the plurality of sensors and the plurality of sensor heads) are attached to the base member 101 at fixed intervals in the circumferential direction of the base member 101 within the same surface as the surface A-A'. The plurality of magnetic sensors (the plurality of sensor heads) 103 are arranged within the same surface as the surface in which the plurality of electrodes 102 are arranged (FIG. 3). The arrangement of the magnetic sensors (sensor heads) 103 can be variously changed.

Also, in the present embodiment, an optical pumping atomic magnetic sensor having ultra-high sensitivity at room temperature is used as the magnetic sensor 103. The optical pumping atomic magnetic sensor can observe a magnetic field of the same degree (the order of $10^{-15}$ Tesla (T)) as that of a superconducting quantum interference device (SQUID) requiring a cryogenic state.

As illustrated in FIG. 4, the alternating current input unit 201 controls an alternating current drive circuit 201A and causes an alternating current to flow between two electrodes 102 among the plurality of electrodes 102. The alternating current drive circuit 201A is a circuit having an alternating current power supply and a constant current circuit (or a constant voltage circuit) and can output an alternating current of a high frequency (e.g., the order of several kHz to several MHz) according to control by the alternating current input unit 201. Thereby, because a component of the alternating current emitted from the electrode 102 to the air is high, it is possible to cause the alternating current to flow inside the measurement object person X without directly attaching the electrode 102 to the body surface of the measurement object person X. Also, it can be seen that a change in impedance is significant in the above-described frequency band when a human body serves as a measurement object (see FIG. 11(*b*)).

Also, although not illustrated, the alternating current input unit 201 includes a switching unit capable of selecting and connecting an alternating current drive circuit 201A and two arbitrary electrodes 102 of the plurality of electrodes 102. The alternating current input unit 201 performs a process of causing an alternating current to flow through the measurement person X while sequentially switching a connection of the alternating current drive circuit 201A and each of the plurality of electrodes 102.

As described above, the alternating current input unit 201 inputs an alternating current via the electrodes 102 arranged at a plurality of positions surrounding a specific tomographic surface of the measurement object person X.

Also, as illustrated in FIG. 4, the magnetic field information acquisition unit 202 is connected to the magnetic sensors 103 and acquires intensities of magnetic fields detected by the magnetic sensor 103 as data (magnetic field intensity information). Also, although not illustrated, the magnetic field information acquisition unit 202 is also connected in parallel to all the magnetic sensors (the sensor cells and the sensor heads) 103 and can simultaneously acquire intensities of magnetic fields generated at positions at which the magnetic sensors 103 are arranged. Also, a circuit necessary to acquire the intensity of the magnetic field as electrical data (magnetic field intensity information) such as a band pass filter, an amplifier, or an analog/digital (A/D) converter is inserted into the connection between the magnetic sensor 103 and the magnetic field information acquisition unit 202.

As described above, the magnetic field information acquisition unit 202 acquires the magnetic field intensity information indicating intensities of magnetic fields at a plurality of positions surrounding a specific tomographic surface via the magnetic sensors 103 arranged around the same tomographic surface as that of the specific tomographic surface of the measurement object person X surrounded by the electrodes 102

[Operation Principle of Detection Unit]

Figure 5:
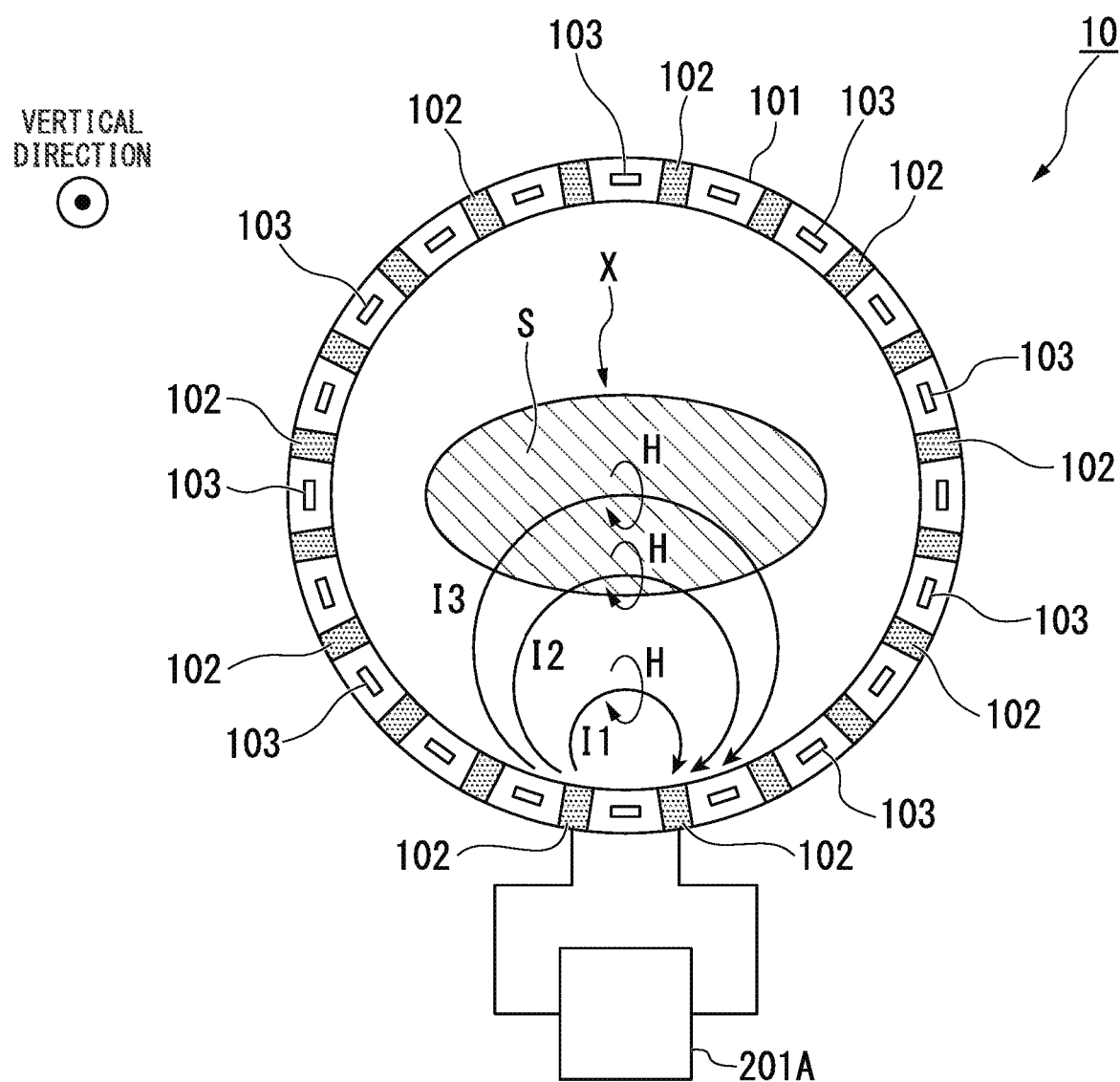
FIG. 5 is a diagram illustrating functions of an electrode and a magnetic sensor according to the first embodiment.

FIG. 5 is a diagram illustrating functions of an electrode and a magnetic sensor according to the first embodiment.

The case in which the alternating current input unit 201 controls the alternating current drive circuit 201A to cause an alternating current to flow between a pair of adjacent electrodes 102 is considered. When the frequency of the alternating current has the order of several MHz, the alternating current is generated to be widened in an arc in the air between the adjacent electrodes 102 as illustrated in FIG. 5. Thereby, the alternating current (alternating currents I1, I2, etc.) is also input inside the measurement object X. The alternating currents I1, I2, etc. input to the measurement object X have values according to transmission paths inside the measurement object person X.

More specifically, because blood or the like included in the measurement object person X is an electrolyte, electrical impedance is lower inside the measurement object person X than in the air. Accordingly, the alternating current emitted from a position between two electrodes 102 to the air is assumed to flow inside the measurement object person X having lower electrical impedance. Then, for example, the alternating currents I2, I3, etc. generally have a larger current value when the measurement object person X is in their fields than when the measurement object person X is not in their fields. Also, even the inside of the measurement object person X, for example, an alternating current passing through an air-filled lung has a smaller current value.

As described above, an alternating current generated between certain electrodes 102 has a current value according to a distribution of electrical impedance inside the measurement object X.

Also, as illustrated in FIG. 5, magnetic fields H are generated around the alternating currents (the alternating currents I1, I2, etc.). The intensity of the magnetic field H is proportional to the generated alternating current value. The magnetic field information acquisition unit 202 detects intensities of the magnetic fields H at positions via the magnetic sensors (the sensor cells and the sensor heads) arranged on the circumference of the base member 101.

The image generation unit 203 to be described below generates a tomographic image of the tomographic surface S (a tomographic surface for the surface A-A' of the measurement object person X) within the same surface as those of the electrodes 102 and the magnetic sensors 103 on the basis of information about the intensities of the magnetic fields H detected by the magnetic sensors 103 acquired by the magnetic field information acquisition unit 202 here.

Also, the frequency of the input alternating current has the order of several kHz to several MHz so that highly precise measurement is enabled when a human body is a measurement object as described above (see FIG. 11). Thus, a magnetic field generated on the basis of the alternating current oscillates at the same frequency. Therefore, in the present embodiment, by using the optical pumping atomic magnetic sensor having high-ultra sensitivity as the magnetic sensor 103, it is possible to precisely detect the intensity of the magnetic field even for the magnetic field oscillating at a relatively high frequency (the order of several MHz). The above-described numeric value is an example and the present invention is not limited thereto.

The form of the magnetic sensor 103 is not limited to the optical pumping atomic magnetic sensor. As the magnetic sensor 103, preferably, a so-called high-sensitivity magnetic sensor is used. In an example, the magnetic sensor 103 can detect the magnetic field H of the order of at least several kHz with high precision. The above-described numeric value is an example and the present invention is not limited thereto. For example, one selected from among various types such as a magnetic impedance (MI) sensor (a magnetic impedance element sensor) and a superconducting quantum interference device (SQUID) can be used as the magnetic sensor 103.

[Processing Flow of CPU]

Figure 6:
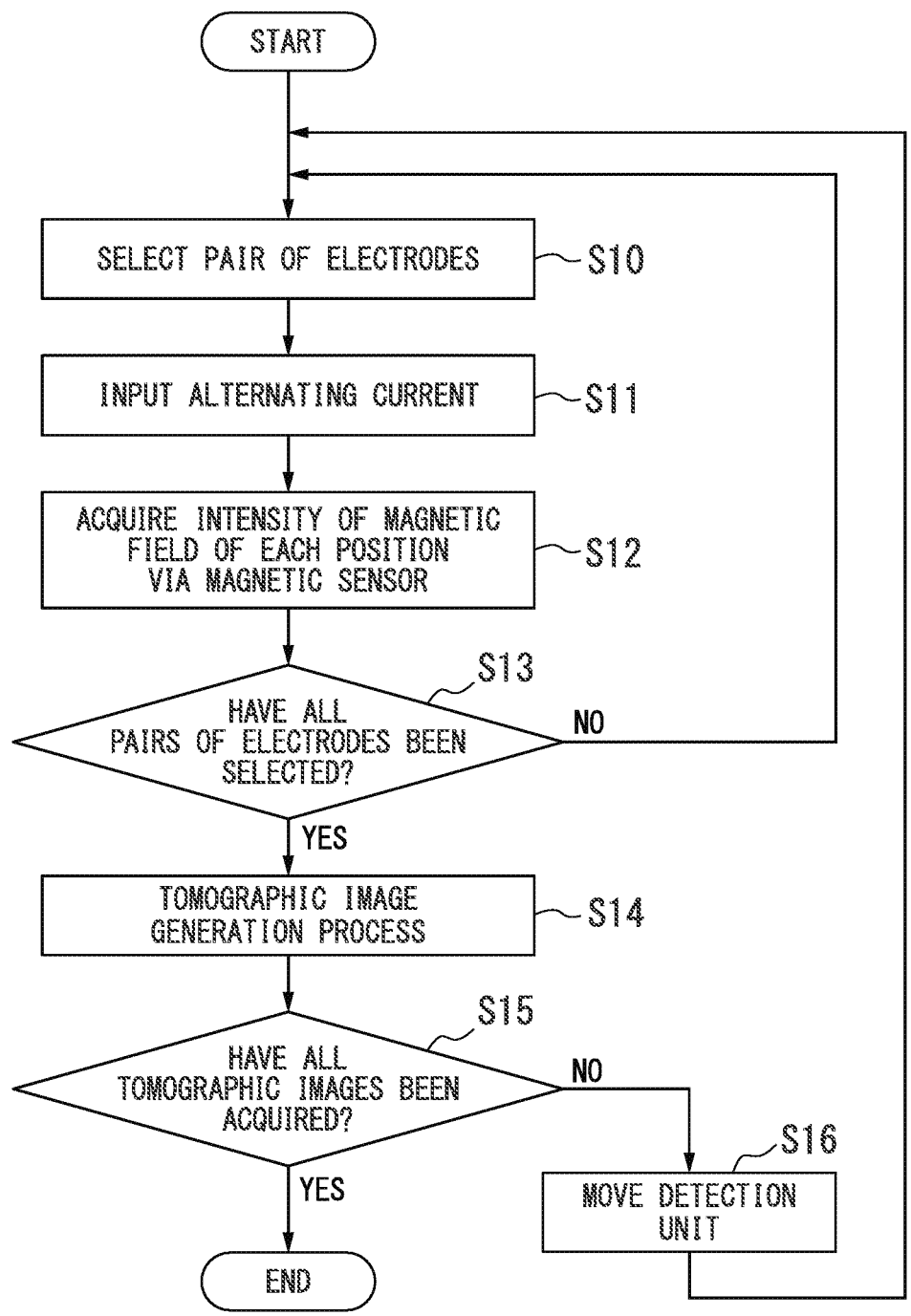
FIG. 6 is a flowchart illustrating a processing flow of a CPU according to the first embodiment.

FIG. 6 is a flowchart illustrating a processing flow of a CPU according to the first embodiment.

Hereinafter, the processing flow executed by the CPU 200 will be sequentially described with reference to FIG. 6 in a measurement procedure of the image generation apparatus 1 according to the present embodiment.

First, when an input operation of a measurement start is received from the operator via the operation input unit 212, the alternating current input unit 201 selects a pair of adjacent electrodes 102 and is connected to the alternating current drive circuit 201A (FIG. 4) (step S10). Next, the alternating current input unit 201 inputs a predetermined control signal to the alternating current drive circuit 201A and causes an alternating current having a set frequency and output intensity to be generated between the selected electrodes 102 (step S11). Thereby, an alternating current having a predetermined intensity (alternating currents I1, I2, etc. (FIG. 5)) is input inside the measurement object person X.

The magnetic field information acquisition unit 202 receives detection signals in parallel from all the magnetic sensors (the sensor cells and the sensor heads) 103 (output signals from the sensors) during inputs of alternating currents and acquires magnetic field intensity information indicating intensities of magnetic fields at each position (step S12). Thereby, the magnetic field information acquisition unit 202 acquires intensities of magnetic fields generated on the basis of alternating currents input by the alternating current input unit 201 at positions at which the magnetic sensors 103 are arranged. The magnetic field information acquisition unit 202 temporarily stores the acquired magnetic field intensity information in a storage region (the RAM 210, the HDD 211, etc.).

When the magnetic field information is acquired between a pair of adjacent electrodes 102, the alternating current input unit 201 selects another pair of adjacent electrodes 102 and inputs an alternating current. The alternating current input unit 201 iterates the above-described process until all pairs of electrodes are selected (step S13). Thereby, the magnetic field information acquisition unit 202 acquires magnetic field intensity information about intensities of magnetic fields in a set of all adjacent electrodes 102.

When the magnetic field intensity information about all the pairs of electrodes 102 is acquired (step S13: YES), the image generation unit 203 refers to the magnetic field intensity information acquired and stored by the magnetic field information acquisition unit 202 to generate a tomographic image of the measurement object person X (step S14). In an example, a technique similar to conventionally known EIT measurement can be used for a technique of generating a tomographic image of the measurement object person X on the basis of the magnetic field intensity information acquired in step S12.

Here, a technique of a process of generating the tomographic image in step S14 will be briefly described. First, in the case of the conventional EIT measurement, a plurality of electrodes are generally attached to a body surface. While a constant current (generally, an alternating current having the order of several kHz) flows between certain selected electrodes, a resistivity distribution in the tomographic surface of the measurement object person is acquired by sequentially measuring a potential difference between other electrodes. In the conventional EIT measurement, the tomographic image is generated using, for example, a known back projection method, on the basis of the resistivity distribution.

To reconfigure an image of EIT in real time, it is assumed that (1) a boundary of a measurement object is circular, (2) electrodes are arranged at equal intervals, (3) an initial conductivity distribution is uniform, (4) a conductivity change is small, and (5) an object is two-dimensional. First, when a sensitivity matrix S defined using a theory of Geselowitz is used, a relationship between a voltage change $\Delta g$ and a conductivity change $\Delta c$ which are measured is as follows.

$$\Delta g = S \Delta c \qquad (1)$$

Here, $\Delta c$ denotes a change amount when a part of a uniform conductivity distribution $c_u$ is changed to c, $\Delta g$ denotes a change amount when a voltage measured in a boundary according to $\Delta c$ is changed from $g_u$ to g. Each sensitivity coefficient is as follows.

$$S_{dre} = -\int_e \nabla \Phi_d \cdot \nabla \Phi_r dV \qquad (2)$$

Here, when a drive electrode and a receive electrode of each set are in a measurement object e, a potential gradient occurring in the receive electrode is denoted by $\nabla_{\varphi_d}$ and a potential gradient occurring in the drive electrode by conversely applying the same current to the receive electrode is denoted by $\nabla_{\varphi_r}$. The sensitivity coefficient S is obtained by assuming that a potential of a point positioned at distances r1 and r2 from a pair of electrodes of two points is $\varphi = (r1)^{-1} - (r2)^{-1}$ in a finite element method. Because it is difficult to significantly obtain an inverse matrix of S, the following result is given when an image is reconfigured as a change rate.

$$\Delta c_n = F^t (FF^t)^+ \Delta g_n \qquad (3)$$

Here, F denotes a normalized sensitivity matrix and denotes a change rate for a certain reference value shown in $\Delta g_n = g/g_{ref}$ and $\Delta c = c/c_{ref}$. That is, the reconfigured image shows a change rate distribution of conductivity. Also, in Equation (3), the symbol "+" denotes a pseudo inverse matrix of a matrix to which "+" is attached.

Because it is significantly difficult to solve an inverse problem of a magnetic field system, an image analysis technique in the above-described EIT is used from the fact that there is a proportional relationship between a change rate of a magnetic field and a change rate of conductivity which are measured in the present embodiment.

A voltage V between electrodes measured in the EIT is represented as in Equation (4).

$$V = \frac{l}{\sigma \cdot s} \times I \qquad (4)$$

Here, "$\sigma$" denotes conductivity of the measurement object (the measurement object person X) (units: S/m and resistivity is $\rho = 1/\sigma$), "l" and "s" denote a length (units: m) and a cross-sectional area (units: m$^2$) when the measurement object is considered to be a rectangular solid, and "I" denotes a current flowing through the measurement object (units: A). That is, if the impedance of the measurement object does not change during measurement, a potential difference V is proportional to the current I.

On the other hand, the magnetic field intensity "H" and the current "I" are generally known to satisfy the relationship of Equation (5).

$$H = \frac{I}{2\pi r} \text{[A/m]} \quad (5)$$

That is, the magnetic field intensity H (units: A/m) at a point separated by a distance "r" (units: m) from a direction in which the current I flows in a perpendicular direction is obtained as in Equation (5) and thereby the magnetic field intensity H and the current I are known to be in a proportional relationship.

Therefore, because the potential difference V and the magnetic field intensity H are also in the proportional relationship, it is possible to acquire an equivalent tomographic image even when an input for the "potential difference V" is replaced with the "magnetic field intensity H" as it is in a known inverse projection method.

Also, a tomographic image generation process to be executed by the image generation unit 203 is not limited to a technique using the inverse projection method used in the above-described EIT measurement and another technique may be used. For example, a technique of solving the inverse problem of the magnetic field system may be used on the basis, for example, the acquired magnetic field intensity information.

When the tomographic image is generated in step S14, the image generation unit 203 outputs the generated tomographic image to the image display unit 213. The operator can perform diagnosis while viewing the tomographic image displayed on the image display unit 213.

When a process of generating one tomographic image is completed, the drive control unit 204 subsequently controls the drive of the drive unit 11. Specifically, the drive control unit 204 determines whether all tomographic images for the measurement object person X have been acquired (step S15). Also, a position of a tomographic surface S for which a tomographic image is acquired, the number of acquisitions, or the like is assumed to be determined at the time of a first setting input by the operator.

When all the tomographic images have not been acquired (step S15: NO), the drive control unit 204 causes the detection unit 10 to be moved in an up/down direction by outputting a predetermined instruction signal to the drive unit 11 (step S16). Thereby, the drive unit 11 changes a relative position of the detection unit 10 with respect to the measurement object person X.

In step S16, the relative position of the detection unit 10 with respect to the measurement object person X is changed, the alternating current input unit 201, the magnetic field information acquisition unit 202, and the image generation unit 203 iterate processes of the above-described S10 to S14. Thereby, it is possible to further acquire a tomographic image for a different tomographic surface of the measurement object X.

In step S16, the CPU 200 ends the process when the scheduled acquisition of all the tomographic images ends (step S15: YES).

[Operations and Effects]

As described above, an operation of attaching a plurality of electrodes to a body surface of the measurement object person X is necessary in the case of the conventional EIT measurement.

On the other hand, in the image generation apparatus 1 according to the present embodiment, as described using FIGS. 3 to 5, etc., all of the plurality of electrodes 102 serving as an output destination of an alternating current input to the measurement object person X and the plurality of magnetic sensors (the plurality of sensors and the plurality of sensor heads) 103 which detect the alternating current as a magnetic field intensity are arranged at positions spaced apart from the measurement object person X. The plurality of electrodes 102 and the plurality of magnetic sensors (the plurality of sensors and the plurality of sensor heads) 103 are arranged in non-direct contact with the surface of the measurement object X. Thereby, it is possible to acquire a tomographic image for a desired tomographic surface of the measurement object person X while the measurement object person X, the electrodes, etc. are fully in a non-contact state (a non-direction contact state).

Thereby, it is possible to not only reduce a burden on an operation in which the operator attaches the electrodes, but also reduce a physical burden on the measurement object person X. The "non-direct contact with the surface of the measurement object X" includes a state in which another physical object is interposed between the electrodes 102/the magnetic sensors 103 and the body surface of the measurement object person and includes, for example, a state in which the electrodes 102/the magnetic sensors 103 are arranged on an outer surface of the clothing worn by the measurement object person. Additionally and/or alternatively, the detection unit 10 can be a type of attachment to the measurement object (the measurement object person). For example, the detection unit 10 can have a configuration in which at least some of the electrodes 102 and the magnetic sensors 103 are provided in the base member 101 formed to be worn by the measurement object person (for example, a band type, a cap type, a helmet type, or the like).

Also, although an example in which measurement is performed while the detection unit 10 surrounding the girth of the measurement object person X moves in the vertical direction in a state in which the measurement object person X stands in FIG. 3 or the like in the present embodiment, other embodiments are not limited to such a form. For example, the image generation apparatus 1 may have a form in which the detection unit 10 is moved in a horizontal direction in a state in which the detection unit 10 surrounds the measurement object person X as a state in which the measurement object person X lays on a dedicated bed or the like. Thereby, it is possible to acquire a tomographic image without imposing a physical burden on the measurement object person X even in a situation in which it is difficult for the measurement object person X to raise his/her body.

Also, in the case of the conventional EIT measurement, the case in which electrical impedance may change according to a state of a body surface (the presence/absence of sweat) on its contact surface and an error occurs in a measurement result is assumed.

In this regard, because a contact surface (a body surface) between the electrodes 102 and the measurement object person is absent, the image generation apparatus 1 according to the present embodiment can eliminate an error factor according to a state of the contact surface.

Also, in the present embodiment, the electrodes 102 are formed of a non-magnetic material as described above. Thereby, the presence of the electrodes 102 can minimize an influence on detection of the magnetic field strength by the magnetic sensors 103. Thereby, each magnetic sensor 103 may precisely detect an intensity of a magnetic field generated at its position without depending upon a positional relationship with the electrodes 102 in the base member 101.

According to the above image generation apparatus 1 according to the first embodiment, it is possible to more easily and precisely acquire a tomographic image of an object.

Also, the image generation apparatus 1 according to the first embodiment can be further modified as follows.

Figure 7:
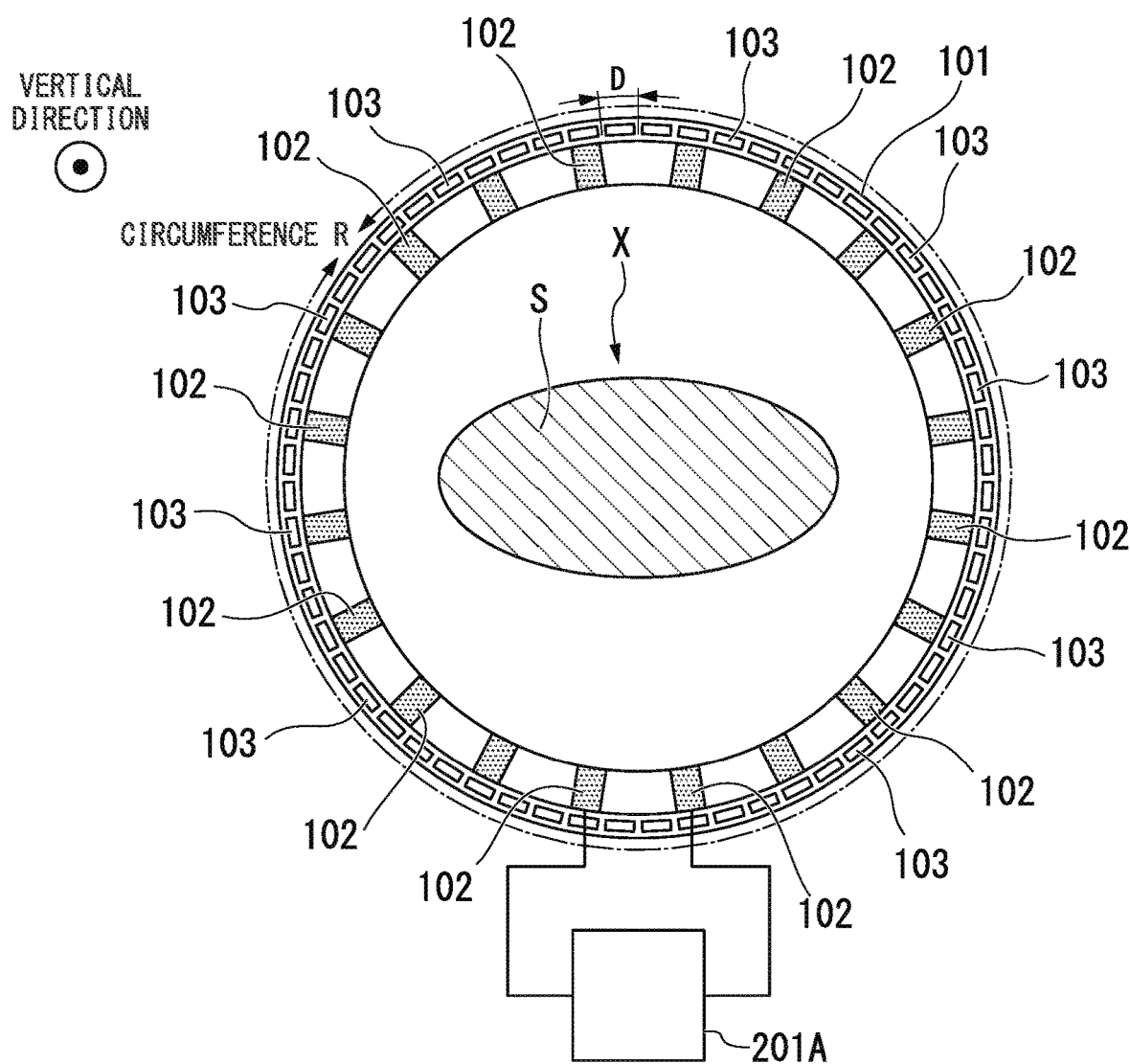
FIG. 7 is a diagram illustrating a structure of a detection unit according to a modified example of the first embodiment.

FIG. 7 is a diagram illustrating a structure of a detection unit according to a modified example of the first embodiment.

In the image generation apparatus 1 according to the first embodiment, an optical pumping atomic magnetic sensor is used as the magnetic sensor 103. Thereby, it is possible to precisely detect an intensity of a magnetic field at room temperature even in the magnetic field oscillating on the order of several kHz to several MHz. That is, because it is possible to exclude all components necessary for use at cryogenic temperature like the SQUID, it is possible to reduce a size of an individual magnetic sensor 103. In this case, as illustrated in FIG. 7, a number of magnetic sensors 103, as many as possible, may be arranged within the constraints according to an individual size regardless of the arrangement of the electrodes 102.

Specifically, the number of magnetic sensors 103 arranged in a circumferential direction of the base member 101 may be determined on the basis of only a length D[m] of a width direction of one of the magnetic sensors 103 and a circumference R[m] of the base member 101 (e.g., Number=R/D).

Thereby, it is possible to increase the number of detection positions of the magnetic field (i.e., an amount of information about the intensity of the magnetic field) as much as possible in a limited size. It is possible to acquire a tomographic image with higher precision by increasing the resolution of the tomographic image.

Also, in this case, as in the first embodiment, the electrodes 102 may be formed of a non-magnetic material.

Also, a processing flow to be executed by the CPU 200 according to the first embodiment is not limited to the processing flow illustrated in FIG. 6. That is, the CPU 200 may acquire magnetic field intensity information in any procedure as long as the magnetic field intensity information in an information amount necessary to generate a tomographic image on the basis of an image generation process (e.g., an inverse projection method or the like) used in the EIT measurement is acquired.

Figure 8:
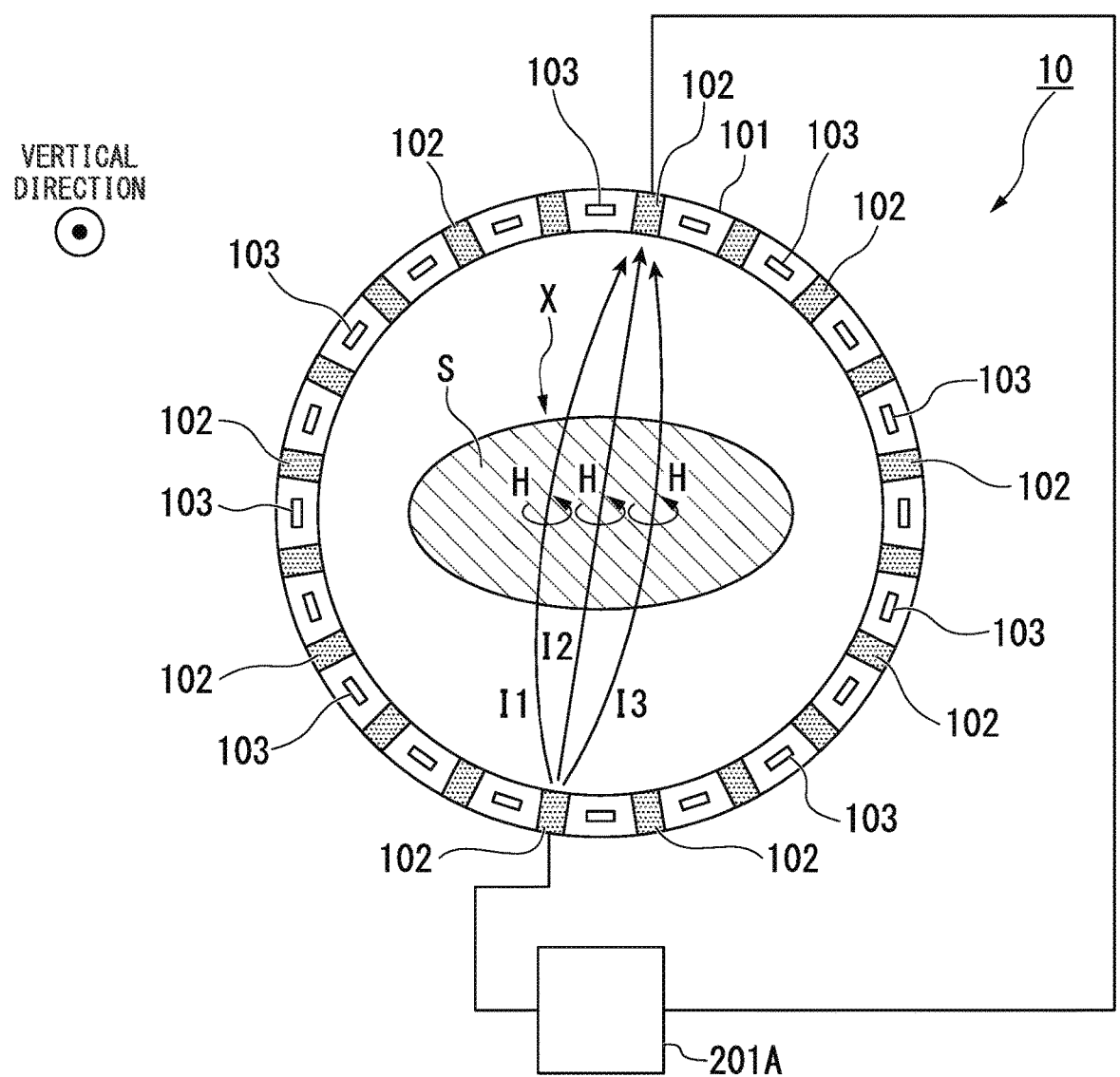
FIG. 8 is a diagram illustrating functions of the electrode and the magnetic sensor according to the modified example of the first embodiment.

FIG. 8 is a diagram illustrating functions of the electrode and the magnetic sensor according to the modified example of the first embodiment.

Also, the CPU 200 (the alternating current input unit 201) according to the first embodiment has been described as inputting an alternating current while sequentially selecting pairs of electrodes 102 adjacent to each other (steps S10 and S11 (FIG. 6)). However, the alternating current input unit 201 according to another embodiment further includes a combination other than a pair of adjacent electrodes 102 to input an alternating current. For example, the alternating current input unit 201 may select one electrode 102 and another electrode 102 located at a position opposite to the one electrode 102 to output the alternating current between the electrodes 102.

Also, in FIG. 5, it can be seen that an alternating current generated between the electrodes 102 adjacent to each other flows as a large current in the vicinity thereof, but an amount of current decreases as a distance from the electrodes 102 increases. Therefore, when the alternating current is generated only between the adjacent electrodes 102, a current flowing through the inside of the measurement object X is weak as compared with an amount of current flowing through a side close to the body surface of the measurement object X. Thus, a tomographic image acquired on the basis of only the alternating current generated between the electrodes 102 adjacent to each other is reproduced with high precision for a region close to the body surface in a tomographic surface S, but the precision of reproduction may be degraded with respect to a deep region separated from the body surface.

Therefore, as illustrated in FIG. 8, for example, an amount of current passing through a deep region within the body of the measurement object person X is increased by causing an alternating current I1 or the like to flow while sequentially selecting pairs of opposite electrodes 102. The magnetic field information acquisition unit 202 can precisely reproduce a deep region separated from the body surface by acquiring a magnetic field generated on the basis of a current distribution.

Also, an alternating current may be input by a combination of pairs of two other arbitrary electrodes 102 as well as a pair of electrodes 102 adjacent to each other or a pair of opposite electrodes 102.

Also, in the image generation apparatus 1 according to the first embodiment, the detection unit 10 is in a state in which a plurality of electrodes 102 and a plurality of magnetic sensors 103 are arranged on the same surface (the surface A-A' (FIG. 3)). Thereby, it is possible to acquire a magnetic field generated on the basis of an alternating current flowing between the electrodes 102 at a high intensity and improve the precision of a tomographic image generated on the basis of the magnetic field. However, the present invention is not limited to such a form in the image generation apparatus 1 according to another embodiment. For example, the detection unit 10 may be a form in which a plurality of electrodes 102 and a plurality of magnetic sensors 103 are arranged on different surfaces. Also, the image generation apparatus 1 according to another embodiment may be a form having a base member (an annular housing) 101 on which the plurality of electrodes 102 are arranged and a base member (a housing) on which magnetic sensors 103 are arranged.

Second Embodiment

Next, an image generation apparatus 1 according to the second embodiment will be described.

Figure 9:
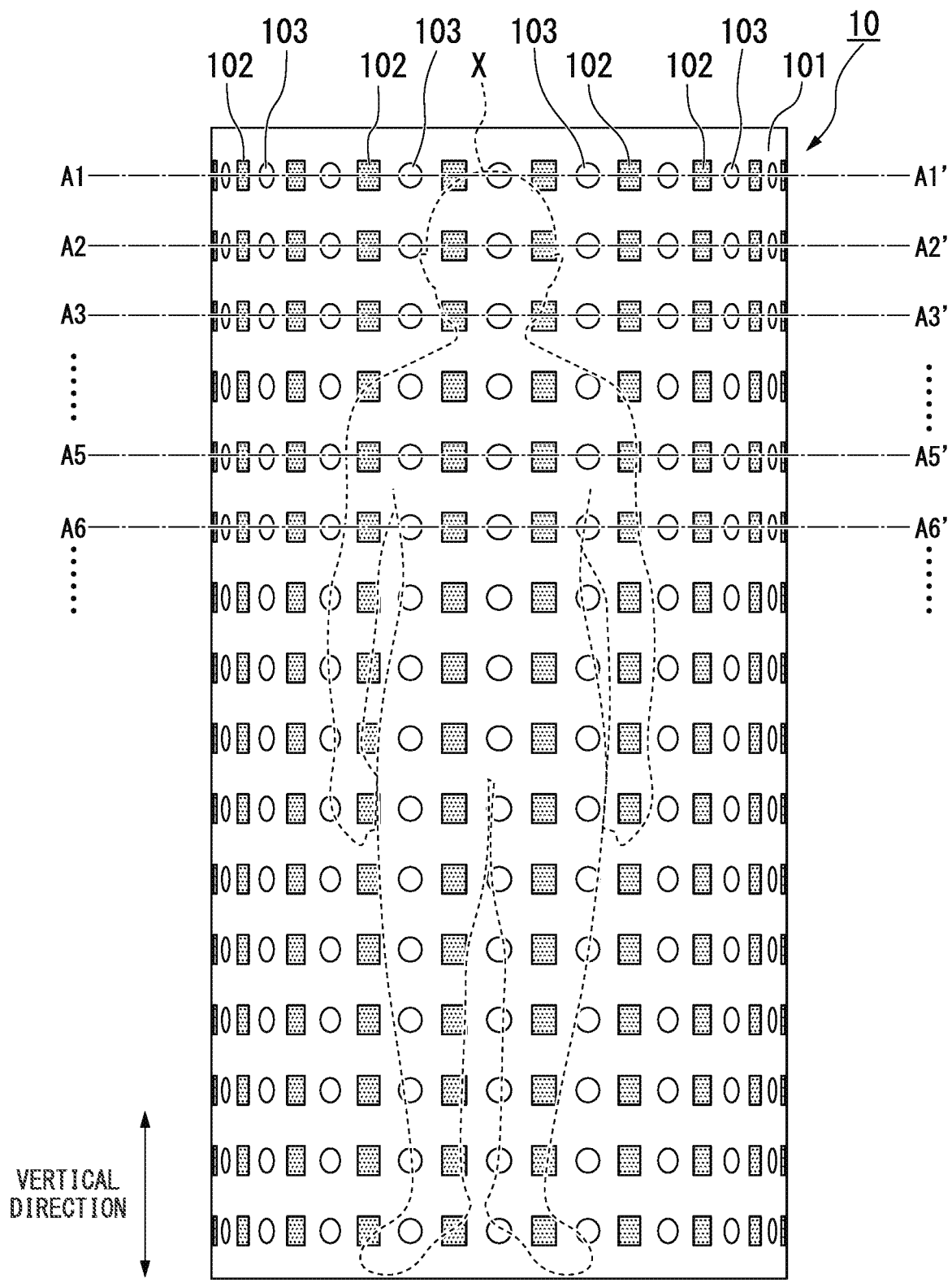
FIG. 9 is a diagram illustrating a structure of a detection unit according to a second embodiment.

FIG. 9 is a diagram illustrating a structure of a detection unit according to a second embodiment.

The image generation apparatus 1 according to the first embodiment has been described as a form in which the annularly formed detection unit 10 surrounds a standing measurement object person X and acquires a plurality of tomographic images of the measurement object person X while moving in a vertical direction according to an operation of the drive unit 11.

The detection unit 10 of the image generation apparatus 1 according to the present embodiment is cylindrically formed to generally extend in the vertical direction as illustrated in FIG. 9. The overall body of the measurement object person X is included inside the cylindrically formed detection unit 10.

Also, in the detection unit 10 according to the present embodiment, the plurality of electrodes 102 and a plurality of magnetic sensors 103 are arranged in the vertical direction as illustrated in FIG. 9. A form in which a plurality of electrodes 102 and a plurality of magnetic sensors 103 are arranged for each of surfaces A1-A1', A2-A2', ... is similar to that of the first embodiment. Thereby, the image generation apparatus 1 can simultaneously acquire tomographic images of a plurality of positions of the measurement object person X.

Specifically, the alternating current input unit 201 according to the present embodiment can cause an alternating current to flow through all of electrodes 102 belonging to the surface A1-A1', electrodes 102 belonging to the surface A2-A2', ... in parallel.

Also, the magnetic field information acquisition unit 202 according to the present embodiment can simultaneously acquire magnetic field information from all of magnetic sensors 103 belonging to the surface A1-A1', magnetic sensors 103 belonging to the surface A2-A2', .... That is, the magnetic field information acquisition unit 202 can acquire intensities of magnetic fields at a plurality of positions surrounding another tomographic surface different from one tomographic surface simultaneously with intensities of magnetic fields at a plurality of positions surrounding the one tomographic surface of the measurement object person X.

Thereby, the image generation apparatus 1 according to the present embodiment can simultaneously generate tomographic images for tomographic surfaces S of the measurement object person X belonging to the surface A1-A1 A2-A2', ... on the basis of magnetic field intensity information acquired via the magnetic sensors 103 belonging to the surfaces A1-A1', A2-A2', Thereby, it is possible to exclude a means (the drive unit 11) for moving the detection unit 10 in the image generation apparatus 1 according to the first embodiment and to shorten a required time for acquiring a plurality of tomographic images. That is, deviation occurs among the plurality of acquired tomographic images when the measurement object person X moves during movement of the detection unit 10 in the first embodiment, but it is possible to reduce deviation among a plurality of tomographic images and execute diagnosis with higher precision by simultaneously acquiring the plurality of tomographic images as in the second embodiment.

Also, the expression of "simultaneously" used in the above description of the image generation apparatus 1 is not necessarily limited to the meaning of "at exactly the same time," and a time difference may be in a range in which deviation among a plurality of acquired tomographic images is allowed.

Figure 10:
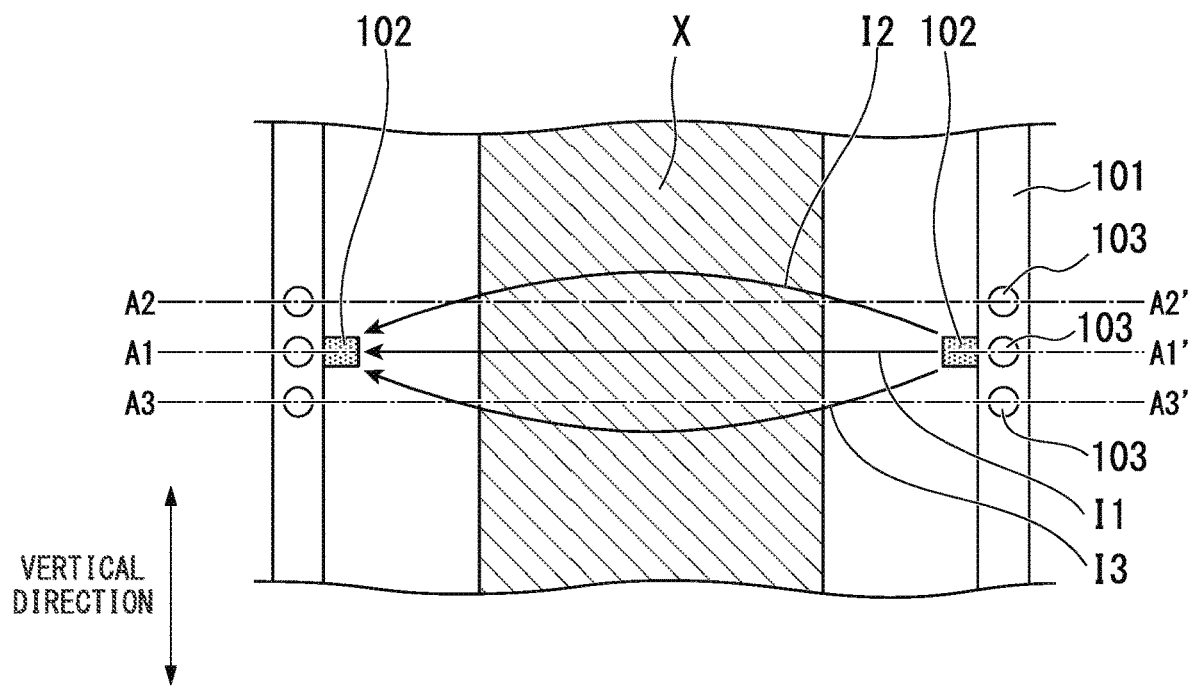
FIG. 10 is a diagram illustrating a function of an image generation unit according to a modified example of the second embodiment.

FIG. 10 is a diagram illustrating a function of an image generation unit according to a modified example of the second embodiment.

The case in which the above-described image generation apparatuses 1 according to the first and second embodiments acquire tomographic surfaces of the measurement object person X belonging to the same surface on the basis of magnetic field intensity information acquired by a plurality of electrodes 102 and a plurality of magnetic sensors 103 located on the same surface has been described.

However, in this case, as illustrated in FIG. 10, an alternating current generated between electrodes 102 includes alternating current components I2 and I3 flowing through the other surfaces A2-A2' and A3-A3' in addition to an alternating current component I1 flowing through the surface A1-A1' to which the electrodes 102 belong. That is, the alternating current flowing between the electrodes 102 actually has a component spread in the vertical direction (the alternating current I2, I3, or the like). If so, information about the other tomographic surfaces (the surfaces A2-A2', A3-A3', etc.) as well as information about the tomographic surface belonging to the surface A1-A1' is mixed in a tomographic image generated on the basis of an intensity of a magnetic field detected by the magnetic sensor 103 belonging to the surface A1-A1'. Therefore, according to the alternating current component spread in the vertical direction, the generated tomographic image may include information about the other tomographic surfaces and may be blurred.

Therefore, the magnetic field information acquisition unit 202 according to the modified example of the present embodiment acquires a magnetic field generated on the basis of an alternating current flowing between the electrodes 102 via the magnetic sensors 103 belonging to another adjacent surface in addition to the magnetic sensors 103 belonging to the same surface as that of the electrodes 102.

For example, as illustrated in FIG. 10, the magnetic field information acquisition unit 202 acquires magnetic fields generated on the basis of alternating currents flowing between the electrodes 102 belonging to the surface A1-A1' via the magnetic sensors 103 belonging to the surface A1-A1' and the magnetic sensors 103 belonging to the surfaces A2-A2' and A3-A3'.

Also, the image generation unit 203 according to the modified example first generates a first intermediate image on the basis of magnetic field intensity information acquired via the magnetic sensors 103 belonging to the surface A1-A1'. Here, the first intermediate image is mainly a tomographic image acquired on the basis of the alternating current component I1, but becomes a blurred image because the alternating current components I2, I3, etc. flowing through the other tomographic surfaces are also included.

Further, the image generation unit 203 generates second and third intermediate images on the basis of the magnetic field information acquired via the magnetic sensors 103 belonging to the surfaces A2-A2', A3-A3'. Here, the second and third intermediate images are mainly tomographic images acquired on the basis of the current components I2 and I3 spread in the vertical direction.

The image generation unit 203 according to the present embodiment performs a process of acquiring differences of the second and third intermediate images from the first intermediate image. Specifically, for example, a process of subtracting the "brightness" of a corresponding pixel in the second and third intermediate images from "brightness" of each pixel of the first intermediate image is performed. The image generation unit 203 acquires a final image calculated as described above as a tomographic image representing a tomographic surface of the measurement object person X belonging to the surface A1-A1'.

As described above, the image generation apparatus 1 according to the modified example of the second embodiment may generate a tomographic image represented by one tomographic surface by combining the first intermediate image generated on the basis of magnetic fields at a plurality of positions surrounding the one tomographic surface and second, third, ... intermediate images generated on the basis of magnetic fields at a plurality of positions surrounding other tomographic surfaces.

Thereby, it is possible to acquire a tomographic image with higher precision because it is possible to exclude information acquired on the basis of alternating current components (the alternating current components I2, I3, etc.) flowing through tomographic surfaces other than a desired tomographic surface.

Also, an example in which the image generation apparatus 1 according to the above-described modified example is based on the second embodiment including the cylindrical detection unit 10 (see FIG. 9) is shown, but the present invention may be applied to the first embodiment, i.e., the image generation apparatus 1 having the annular detection unit 10 (see FIG. 3). In this case, at least a plurality of magnetic sensors 103 are assumed to be arranged in the vertical direction in the annular detection unit 10.

Also, the case in which the image generation apparatus 1 according to the above-described modified example performs a process of subtracting a tomographic image by subtracting the "brightness" for each pixel after the first to third intermediate images are generated has been described, but the first to third intermediate images described here may not be actually generated and displayed. That is, one tomographic image may be generated after pre-subtracting an intensity of a magnetic field which is an observation value of a basis corresponding to the brightness for each pixel of the first to third intermediate images.

Also, the case in which the image generation apparatus 1 according to each embodiment described above acquires a tomographic image according to an alternating current of a predetermined fixed frequency (several kHz to several MHz) has been described, but another embodiment is not limited to this form. For example, the image generation apparatus 1 according to another embodiment may acquire a tomographic image on the basis of alternating currents of a plurality of different frequencies.

Specifically, the alternating current input unit 201 according to another embodiment outputs a frequency designation signal for designating a frequency of an alternating current to the alternating current drive circuit 201A. The alternating current drive circuit 201A outputs an alternating current of a frequency according to the received frequency designation signal.

Also, in this case, the image generation apparatus 1 generates a tomographic image for each frequency of an alternating current output from the alternating current drive circuit 201A and acquires a conductivity distribution of the tomographic surface on the basis of frequency characteristics for each pixel constituting a plurality of obtained tomographic images.

For example, the alternating current input unit 201 first selects one frequency when the processing flow illustrated in FIG. 6 starts. Next, the CPU 200 acquires a tomographic image by executing processes of steps S10 to S14. Thereafter, the alternating current input unit 201 switches the alternating current to another frequency.

As described above, the CPU 200 iterates the processes of steps S10 to S14 while switching a frequency of the alternating current. The image generation unit 203 generates a plurality of tomographic images for each different frequency on the basis of an intensity of a magnetic field generated according to each frequency.

Also, in this case, the CPU 200 further exhibits a function serving as a conductivity calculation unit which calculates a conductivity distribution of a tomographic surface of the measurement object person X on the basis of the plurality of tomographic images generated for each different frequency.

Specifically, the conductivity calculation unit extracts conductivities of positions corresponding to one identical pixel among a plurality of tomographic images generated for each frequency and acquires a frequency characteristic of the conductivity for each pixel. The conductivity calculation unit calculates real components (resistance and conductance) and imaginary components (reactance and susceptance) of the conductivity corresponding to the pixel on the basis of frequency characteristics of the conductivity. Thereby, it is possible to acquire a more detailed tomographic image because it is possible to divide the conductivity distribution in the tomographic surface into a real component and an imaginary component and grasp the real and imaginary components.

Figure 11:
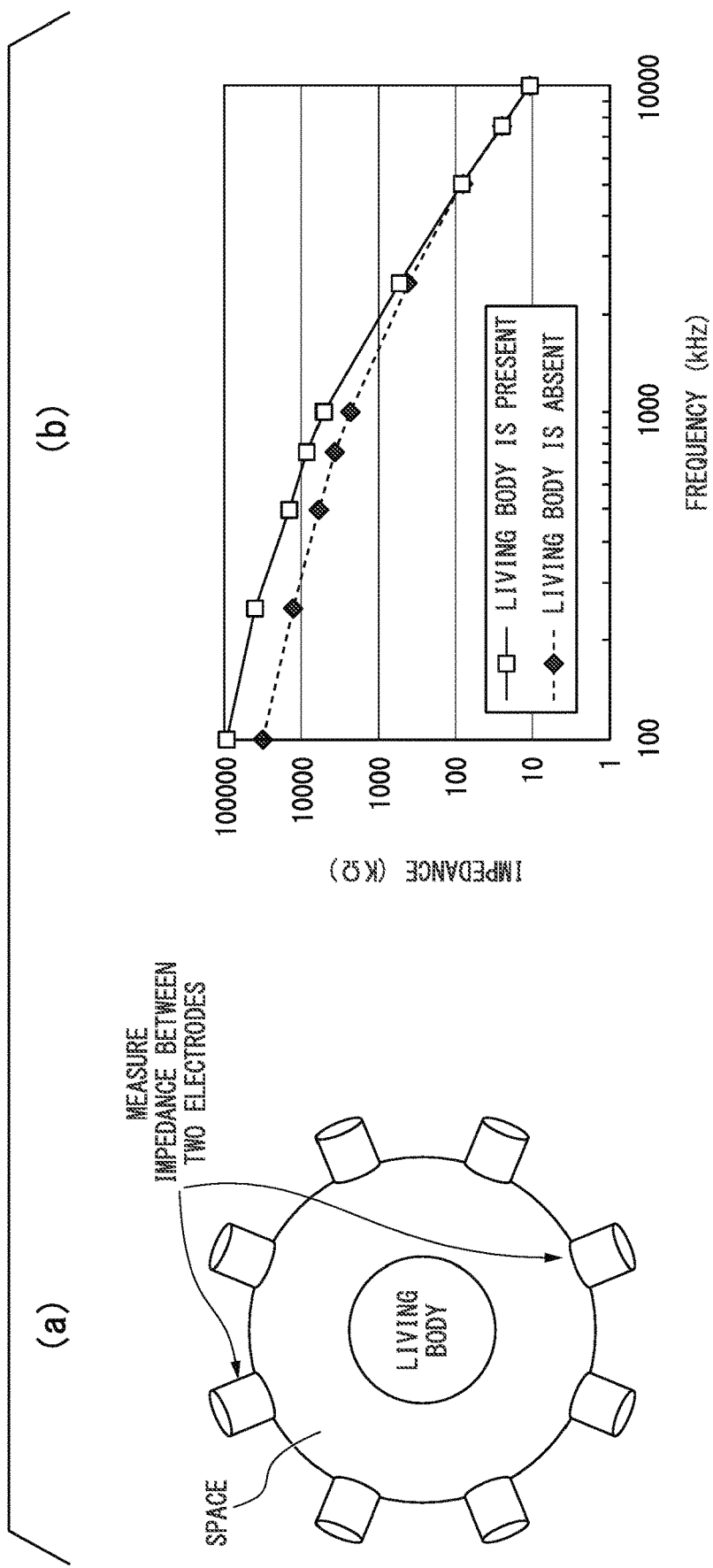
FIG. 11 is a diagram illustrating characteristics of an impedance change according to a living body.

FIG. 11 is a diagram illustrating characteristics of an impedance change according to a living body.

As in FIG. 11(*a*), the case in which a living body (a "fist" in the present experiment) is inserted between two electrodes which are separated in a non-contact type is considered.

The graph illustrated in FIG. 11(*b*) is for the comparison of impedance between two electrodes when the living body is present between the two electrodes and when the living body is not present between the two electrodes. A difference between the presence and absence of the living body is clearly shown when the frequency used in measurement is about several kHz to several MHz according to FIG. 11(*b*). Therefore, it is preferable that a frequency used in the acquisition of a tomographic image of the living body be several kHz to several MHz. Also, because impedance is significantly high and a current flowing through the living body is weak in a region of less than a frequency of 1000 kHz, highly precise measurement may be difficult. Therefore, it is preferable that a frequency to be used in tomographic image generation of the living body be about 1 MHz. In this case, it is possible to detect an intensity of a magnetic field about 1 MHz with high precision using an "optical pumping atomic magnetic sensor" as the magnetic sensor 103.

<Other Modified Examples>

The measurement object person X from which a tomographic image is acquired is arranged inside the annularly formed detection unit 10, for example, as illustrated in FIG. 4, in the image generation apparatus 1 according to each embodiment described above, but the image generation apparatus 1 according to another embodiment is not limited to such a form.

For example, as the modified example of the first embodiment, the magnetic field information acquisition unit 202 may acquire intensities of magnetic fields at a plurality of positions surrounding the periphery of a specific tomographic surface of the measurement object person X. More specifically, the detection unit 10 according to the modified example is attached to a distal end of an endoscope, a catheter, or the like in, for example, a small size in the state illustrated in FIG. 4. The detection unit 10 is inserted inside a body of the measurement object person X along with the endoscope. In this case, the image generation apparatus 1 acquires a tomographic image of a specific tomographic surface via the detection unit 10 surrounding the periphery of the specific tomographic surface within the body into which the detection unit 10 is inserted.

Here, although only alternating currents which travel around the inside of the base member 101 among alternating currents flowing between adjacent electrodes 102 are referred to as alternating currents I1 to I3, for example, in FIG. 5, there is also an alternating current which actually travels around the outside of the base member 101. Therefore, an alternating current which flows between electrodes 102 also changes according to a conductivity distribution of a tomographic surface arranged outside the base member 101. Therefore, the image generation unit 203 can acquire a tomographic image of a tomographic surface surrounding the circumference of the detection unit 10 by executing a process of reconfiguring an image using an intensity of a magnetic field detected from each of the magnetic sensors 103.

According to the image generation apparatus 1 according to the above-described modified example, it is possible to precisely evaluate a local tomographic surface within the body of the measurement object person X because the application of an alternating current and the measurement of an intensity of a magnetic field are performed in a non-contact type from the inside of the body of the measurement object person X.

Next, a conductivity acquisition apparatus obtained by further simplifying the first embodiment and the above-described modified examples will be described.

Figure 12:
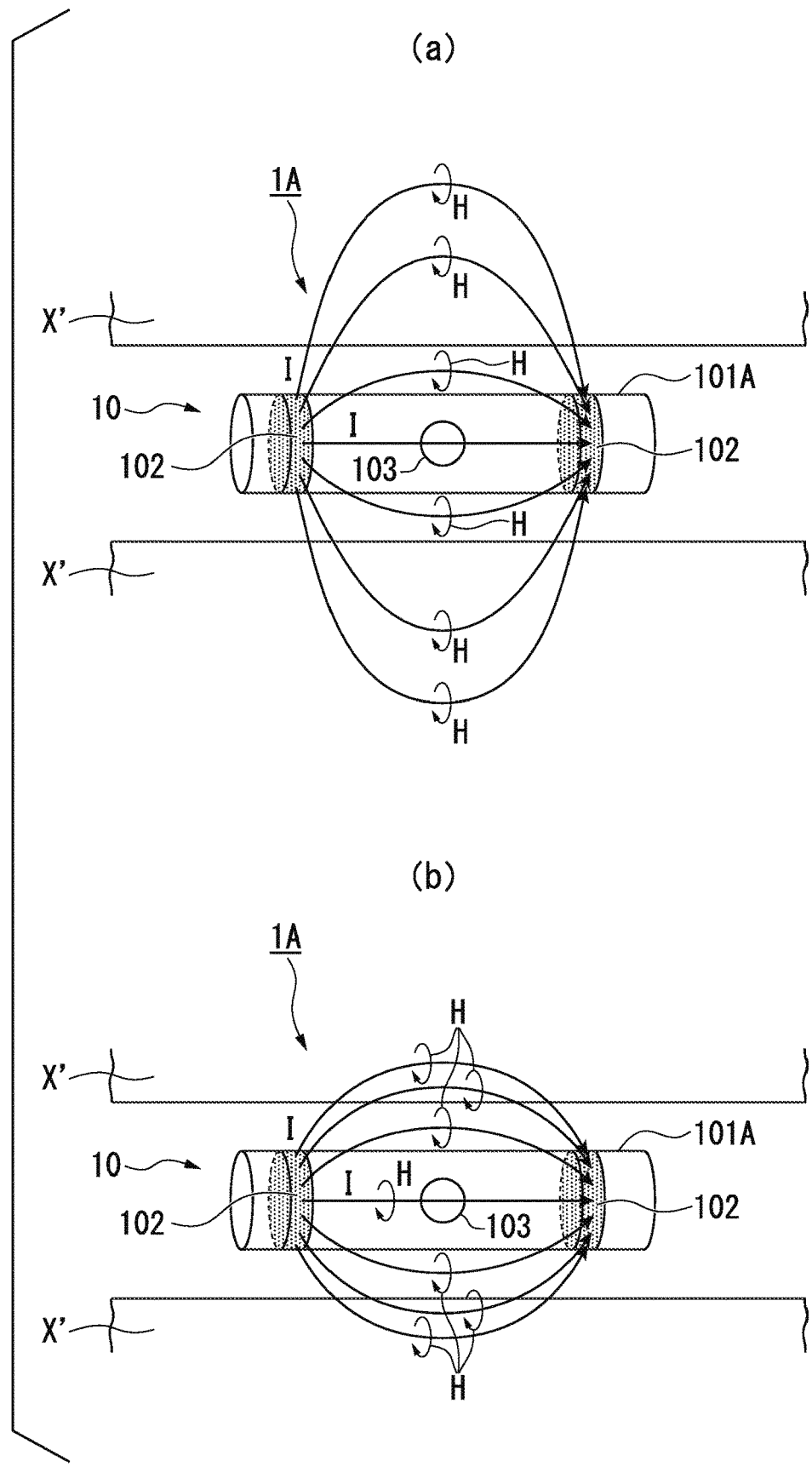
FIG. 12 is a diagram illustrating a function of a conductivity acquisition apparatus according to a modified example of the first embodiment.

FIG. 12 is a diagram illustrating a function of a conductivity acquisition apparatus according to a modified example of the first embodiment.

The conductivity acquisition apparatus 1A according to the present modified example includes the detection unit 10 as illustrated in FIGS. 12 (a) and (b). In an example, specifically, as illustrated in FIGS. 12 (a) and (b), the detection unit 10 includes a pair of electrodes 102 attached in the vicinity of both ends of a base member (a cylindrical housing) 101A and a magnetic sensor 103 arranged between the pair of electrodes 102.

The pair of electrodes 102 are annularly formed along the overall circumference of the base member 101A in a circumferential direction. By forming the pair of electrodes 102 as described above, an alternating current I flowing between the pair of electrodes 102 travels around paths spread in an arc in the air in all orientations of a centrifugal direction of the base member 101A (see FIGS. 12 (a) and (b)).

The pair of electrodes 102 are connected to the alternating current input unit 201 and the alternating current drive circuit 201A (not illustrated in FIG. 12). Also, the magnetic sensor 103 is connected to the magnetic field information acquisition unit 202 (not illustrated in FIG. 12). Also, because the alternating current input unit 201, the alternating current drive circuit 201A, and the magnetic field information acquisition unit 202 have the same function as those of each embodiment described above, description thereof will be omitted. Here, it is preferable for the alternating current input unit 201 to have a function of outputting a frequency designation signal for designating a frequency of an alternating current.

Also, the conductivity acquisition apparatus 1A according to the present modified example includes a conductivity acquisition unit (not illustrated) which acquires conductivity of the measurement object person X around a region in which the magnetic sensor 103 is arranged on the basis of an intensity of a magnetic field acquired by the magnetic field information acquisition unit 202 in place of the image generation unit 203.

FIGS. 12 (a) and (b) illustrates examples in which the base member 101A is inserted into a body inside X' of the measurement object person X. Here, as examples, FIG. 12(a) illustrates the case in which the conductivity of the body inside X' surrounding the detection unit 10 is high and FIG. 12(b) illustrates the case in which the conductivity of the body inside X' surrounding the detection unit 10 is low.

Because an alternating current I which flows through the body inside X' increases when the conductivity of the body inside X' is high, an alternating current I flowing between a pair of electrodes 102 travels around a path widened in a radial direction with respect to an extending axis of the base member 101A as illustrated in FIG. 12(a). Thereby, an intensity of a magnetic field detected by the magnetic sensor 103 is relatively decreased because a magnetic field H generated by the alternating current I is generally far away from the magnetic sensor 103. On the other hand, because an alternating current I which flows through the body inside X' decreases when the conductivity of the body inside X' is low, an alternating current I flowing between a pair of electrodes 102 travels around a path narrowed in a radial direction with respect to an extending axis of the base member 101A as illustrated in FIG. 12(b). Thereby, an intensity of a magnetic field detected by the magnetic sensor 103 is relatively increased because a magnetic field H generated by the alternating current I is generally close to the magnetic sensor 103.

Thereby, the magnetic field information acquisition unit 202 acquires an intensity of a magnetic field according to the conductivity of the body inside X'. Also, the magnetic field information acquisition unit 202 may detect a plurality of intensities of magnetic fields for each different frequency on the basis of frequency control of the alternating current input unit 201.

Also, the above-described conductivity acquisition unit calculates conductivity around the base member 101A on the basis of an intensity of a magnetic field acquired by the magnetic field information acquisition unit 202. In this case, the above-described conductivity acquisition unit calculates conductivity $\sigma$ according to the acquired intensity of the magnetic field using, for example, Equation (4), Equation (5), a predefined length 1, a cross-sectional area s, or the like. Also, the above-described conductivity acquisition unit may calculate a real component and an imaginary component of the conductivity $\sigma$ on the basis of a frequency characteristic of the acquired intensity of the magnetic field.

Also, a medical device such as an endoscope for observing an inside of a human body has been conventionally developed. With this medical device, it is possible to observe a video of the inside by embedding an optical system into a main body and inserting a distal end into the body. However, because the above-described endoscope or the like is operated by optical observation, it is impossible to grasp a characteristic that an optical change (i.e., a change in appearance) is not shown in an observation surface. On the other hand, according to the conductivity acquisition apparatus 1A according to the present modified example, a state of the body inside X' around the detection unit 10 is evaluated on the basis of conductivity at its position. Thereby, the operator can also grasp a symptom not visually apparent in the observation surface according to a difference of conductivity at its position. For example, even when a cancerous cell is located at a position which is not visually apparent, the conductivity acquisition apparatus 1A according to the present embodiment can discover the cancerous cell according to a conductivity difference between the cancerous cell and a normal cell.

Also, because the conductivity acquisition apparatus 1A according to the present modified example can acquire conductivity in a state in which all of the detection unit 10 (the electrodes 102 and the magnetic sensor 103) is arranged at a position separated from an inner wall surface within the body, it is possible to easily acquire conductivity within the body and further contribute to the reduction of a burden on the measurement object person.

Also, because the detection unit 10 according to the present modified example is configured to have only a pair of electrodes 102 and one magnetic sensor 103, the configuration of the detection unit 10 is simplified more than the image generation apparatus 1 according to each embodiment described above and the size reduction and the cost reduction of the apparatus can be promoted.

Also, the conductivity acquisition apparatus 1A according to the present modified example is not limited to a state in which the conductivity acquisition apparatus 1A is attached to a distal end of the endoscope or the catheter and inserted into a body of the measurement object person X (FIGS. 12 (*a*) and (*b*)). Alternatively, the conductivity acquisition apparatus 1A may cause the detection unit 10 to be in the vicinity of a body surface of the measurement object person X and acquire conductivity in the vicinity of the body surface. At least some of the electrodes 102 and the magnetic sensor 103 are arranged in non-direct contact with the body surface in the vicinity of the body surface. Alternatively, at least some of the electrodes 102 and the magnetic sensor 103 can be at least temporarily arranged in direct contact with the body surface.

Also, the conductivity acquisition apparatus 1A is not limited to an annularly formed structure to surround the overall circumference of the base member (the cylindrical housing) 101A in the circumferential direction. Alternatively, the conductivity acquisition apparatus 1A may be formed to surround, for example, only a part of the base member 101A in the circumferential direction (to partially extend in the circumferential direction of the base member 101A). Also, the electrodes 102 are not limited to an annular shape in the conductivity acquisition apparatus 1A. Alternatively, the electrodes 102 may be formed in another shape such as plate shape. In this case, orientations in which plate surfaces of the two electrodes 102 are directed are arranged to be toward an orientation of any of a direction vertical to an extending axis direction of the base member 101A, i.e., the circumferential direction of the base member 101A (and the same orientation). If so, an alternating current particularly strong in a range of a part of the base member 101A in the circumferential direction is emitted in the air. Thereby, the operator can acquire a conductivity distribution of only a desired partial region within the body inside X' surrounding the circumference of the base member 101A by manipulating an orientation of the circumferential direction of the base member 101A to a desired orientation.

Likewise, for the conductivity acquisition apparatus 1A, a direction, a density, or the like of an alternating current may be adjusted by attaching a shield electrode or a guard electrode in the vicinity of a region in which the electrodes 102 are arranged.

Also, in each modified example described above, the "position separated from the measurement object (the measurement object person X)" is assumed to include the meanings of a "position separated from the inner wall surface within the body of the measurement object person X," a "position having a gap from the inner wall surface within the body of the measurement object person X," and a "position arranged in non-direct contact with respect to an inner surface within the body of the measurement object person X."

Also, in the embodiments illustrated in FIGS. 1, 2, etc., the image generation apparatus 1 includes a plurality of electrodes 102; a plurality of magnetic sensors (a plurality of sensor cells and a plurality of sensor heads) 103; and a main body unit (a controller) 20 configured to provide a tomographic image of a measurement object on the basis of an intensity of a magnetic field generated by an alternating current supplied via the electrodes 102, wherein the controller 20 is configured to acquire intensities of magnetic fields via the magnetic sensors 103 in a state in which the electrodes and the magnetic sensors are arranged substantially in non-direct contact with the surface of the measurement object. In another embodiment, the main body unit 20 can be configured to acquire an intensity of a magnetic field via the magnetic sensor 103 in a state in which at least some of the plurality of electrodes 102 and the plurality of magnetic sensors (the plurality of sensor cells and the plurality of sensor heads) are substantially in contact with the surface of the measurement object. In any form, it is possible to implement high flexibility of an arrangement of the electrodes 102 and the magnetic sensors, high operability, simplification of a configuration, etc. Therefore, the image generation apparatus 1 has advantages of the reduction of a burden on the operator or the measurement object person, the reduction of an apparatus cost or an installation space, etc.

Figure 13:
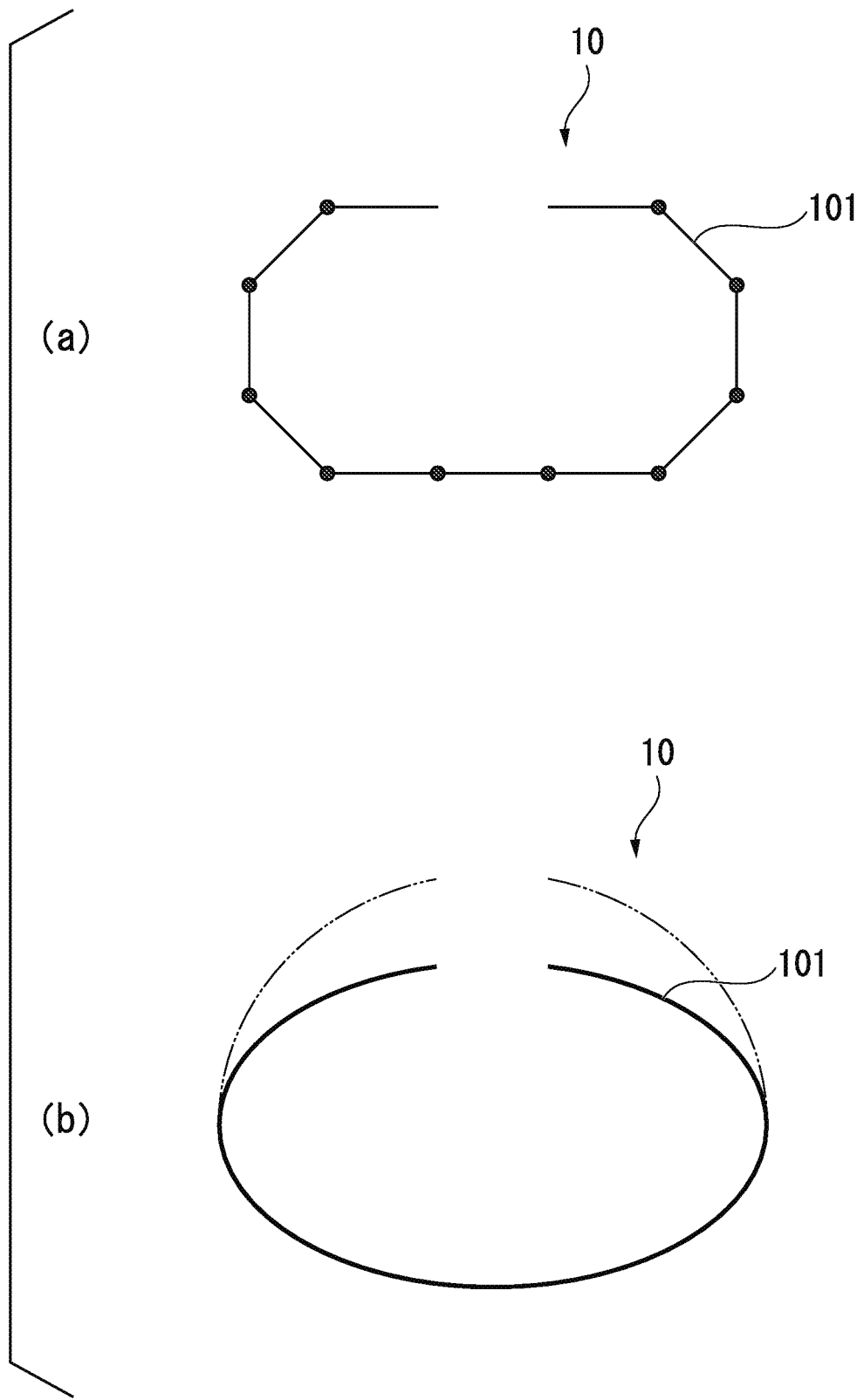
FIG. 13 is a schematic diagram illustrating a detection unit according to another embodiment.

As illustrated in FIGS. 13 (*a*) and (*b*), in an embodiment, the detection unit 10 can include a base member 101 configured to be freely modified. In an example, at least some of a plurality of electrodes and a plurality of magnetic sensors (a plurality of sensor cells and a plurality of sensor heads) are provided in the base member 101 so that at least some of the plurality of electrodes and the plurality of magnetic sensors (see FIG. 3, etc.) move according to motion of the base member 101. The base member 101 can be configured to have at least one joint and at least two beams. Alternatively, the base member 101 can be configured to have a flexible structure having appropriate flexibility and appropriate rigidity. Alternatively, the base member 101 can be configured to have at least one open section and/or configured to be able to be assembled and disassembled. According to modification of the base member 101, it is possible to adjust the arrangement of the electrodes and the magnetic sensors according to the modification of the base member 101. The adjustment of the arrangement of the electrodes and the magnetic sensors is advantageous for the improvement of measurement precision.

Also, in an embodiment, a plurality of magnetic sensors can be arranged so that at least one of the magnetic sensors independently and freely changes a distance from the measurement object. For example, in a state in which a distance (a first distance) from the measurement object in one magnetic sensor (a sensor cell and a sensor head) is uniformly maintained, it is possible to change a distance (a second distance) from the measurement object in at least one other magnetic sensor. As a result, the first distance and the second distance can be substantially the same value. When distances of the plurality of magnetic sensors from the body surface are substantially the same, this is advantageous for the improvement of the measurement precision.

Figure 14:
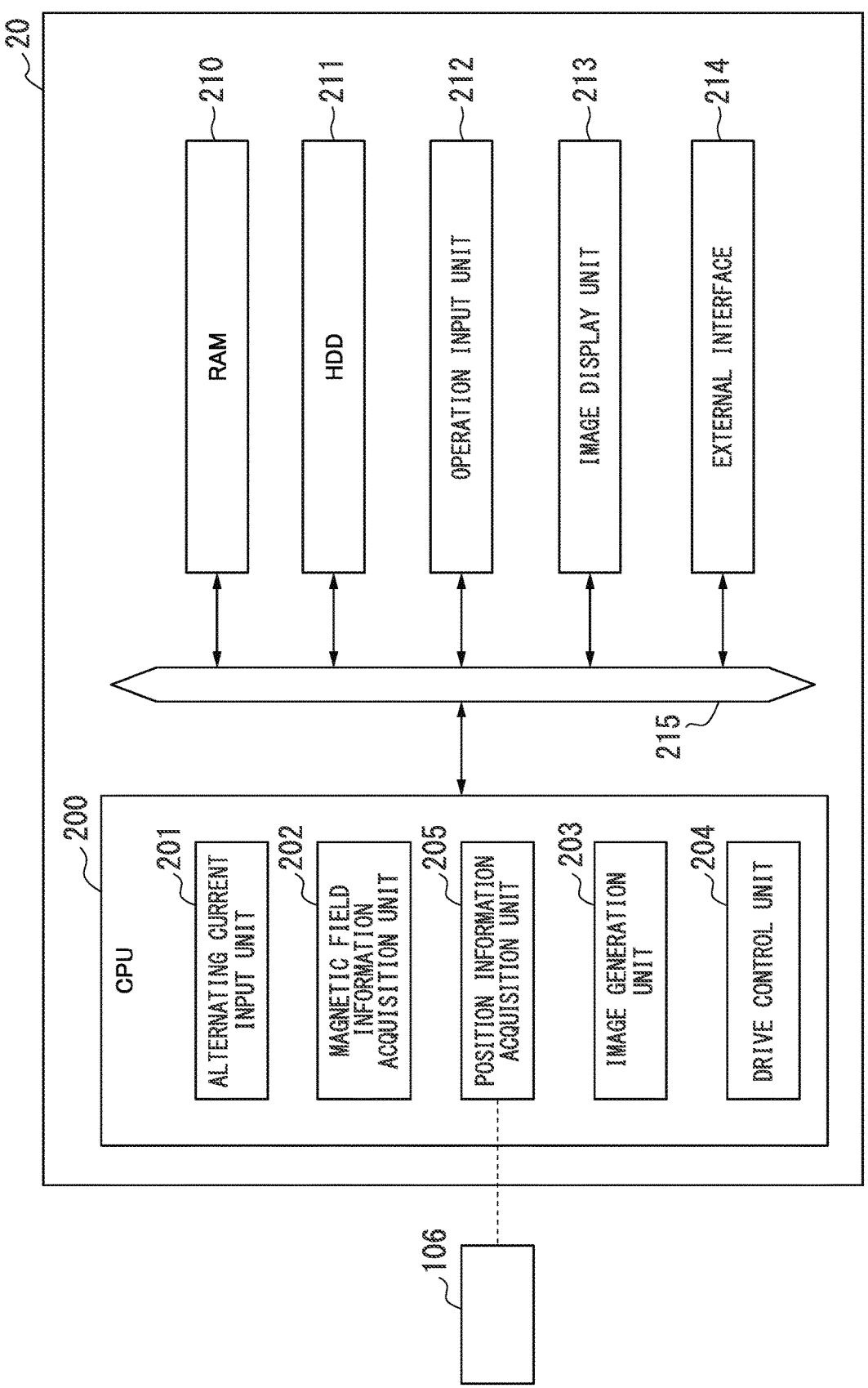
FIG. 14 is a diagram illustrating a functional configuration of a main body unit according to another embodiment.

As illustrated in FIG. 14, in an embodiment, the image generation apparatus 1 includes a position information sensor 106 capable of detecting at least one of (a) a position for a reference point, (b) a distance from the measurement object, and (c) a relative positional relationship with the measurement object, with respect to at least one of the plurality of sensor cells. Alternatively, the position information sensor 106 can be configured to be able to detect at least some of a position, a posture, and a contour (a surface shape) of the measurement object with respect to at least a part of the detection unit 10. Alternatively, the position information sensor 106 can be configured to be able to detect a relatively positional relationship between the detection unit 10 and the measurement object. In the main body unit (the controller) 20, a position information acquisition unit 205 can acquire at least one of (a) a position for a reference point (coordinates for an origin), (b) a distance from the measurement object, and (c) a relative positional relationship with the measurement object, with respect to at least one of a plurality of magnetic sensors (a plurality of sensor cells and a plurality of sensor heads) on the basis of an output signal from the position information sensor 106. On the basis of this position information, control related to at least one of the electrodes and the magnetic sensors can be adjusted. For example, the main body unit 20 can adjust supply control of the alternating current on the basis of an output signal from the position information sensor 106. Alternatively, the main body unit 20 can correct calculation control based on an output signal from the magnetic sensor on the basis of the output signal from the position information sensor 106. The main body unit 20 can calculate an intensity of a magnetic field on the basis of an output from the position information sensor 106 and outputs from the plurality of magnetic sensors. This control is advantageous for the improvement of measurement precision.

Also, a process may be executed by recording a program for implementing a function of the CPU 200 in each embodiment described above on a computer-readable recording medium and causing a computer system to read and execute the program recorded on the recording medium. Also, the "computer system" used here is assumed to include an operating system (OS) and hardware such as peripheral devices. In addition, the "computer-readable recording medium" refers to a storage device including a flexible disk, a magneto-optical disc, a read only memory (ROM), or a portable medium such as a compact disc (CD)-ROM, and a hard disk embedded in the computer system. Furthermore, the "computer-readable recording medium" is assumed to include a medium that holds a program for a constant period of time, such as a volatile memory (a random access memory (RAM)) inside a computer system serving as a server or a client when the program is transmitted via a network such as the Internet or a communication circuit such as a telephone circuit.

Also, the above-described program may be transmitted from a computer system storing the program in a storage device or the like via a transmission medium or transmitted to another computer system by transmission waves in a transmission medium. Here, the "transmission medium" for transmitting the program refers to a medium having a function of transmitting information, such as a network (communication network) like the Internet or a communication circuit (communication line) like a telephone circuit. Also, the above-described program may be a program for implementing some of the above-described functions. Further, the above-described program may be a program, i.e., a so-called differential file (differential program), capable of implementing the above-described function in combination with a program already recorded on the computer system.

Several embodiments according to the invention have been described, but these embodiments are presented as examples and are not intended to limit the scope of the invention. These novel embodiments can be implemented in various other forms, and various omissions, substitutions, and changes can be made in a scope not departing from the spirit of the invention. These embodiments and the modifications are included in the scope or spirit of the invention, and also in the equivalent scope of claims of the invention.

DESCRIPTION OF THE REFERENCE SYMBOLS

1 Image generation apparatus
1A Conductivity acquisition apparatus
10 Detection unit
101 Base member (annular housing)
101A Base member (cylindrical housing)
102 Electrode
103 Magnetic sensor (sensor cell, sensor head)
106 Position information sensor
11 Drive unit
20 Main body unit
200 CPU
201 Alternating current input unit
201A Alternating current drive circuit
202 Magnetic field information acquisition unit
203 Image generation unit
204 Drive control unit
205 Position information acquisition unit
210 RAM
211 HDD
212 Operation input unit
213 Image display unit
214 External interface
215 System bus

The invention claimed is:

1. An image generation apparatus comprising:
a plurality of electrodes configured to convey an alternating current at a high frequency of more than 100 kHz and equal to or less than 10 MHz from a first electrode of the plurality of electrodes, through a measurement object, and to a second electrode of the plurality of electrodes, in use;
a plurality of sensor cells configured to detect an intensity of a magnetic field generated by the alternating current;
a base member on which the plurality of electrodes and the plurality of sensor cells are provided, the base member being configured to maintain an air gap between the electrodes and the measurement object in use so that the alternating current conveyed by the electrodes travels through a volume of air before reaching the measurement object; and
a controller configured to provide a tomographic image of the measurement object based on an intensity of the magnetic field generated by the alternating current, the controller being further configured to acquire the intensity of the magnetic field via the plurality of sensor cells,
wherein the plurality of electrodes are configured to direct the alternating current through the measurement object without being attached to a body surface of the measurement object, and
wherein the base member, the electrodes, and the sensor cells are movable together relative to the measurement object in a predetermined direction.

2. The image generation apparatus according to claim 1, wherein each of the plurality of sensor cells is a part of an optical pumping atomic magnetic sensor or a magnetic impedance element sensor.

3. The image generation apparatus according to claim 1, wherein at least one of the plurality of sensor cells is arranged to independently and freely change a distance from the measurement object.

4. The image generation apparatus according to claim 1, further comprising:
a position information sensor capable of detecting at least one of (a) a position for a reference point, (b) a distance from the measurement object, and (c) a relative positional relationship with the measurement object, with respect to at least one of the plurality of sensor cells,
wherein the controller is configured to calculate the intensity of the magnetic field based on an output from the position information sensor and outputs from the plurality of sensor cells.

5. The image generation apparatus according to claim 1, wherein the plurality of electrodes are positioned to be closer to the measurement object than the plurality of sensor cells.

6. The image generation apparatus according to claim 1, wherein each of the plurality of sensor cells is positioned between two adjacent electrodes.

7. The image generation apparatus according to claim 1, wherein a position of each sensor cell relative to the measurement object is independently adjustable so that each sensor cell is the same distance from the measurement object.

8. The image generation apparatus according to claim 1, wherein each sensor cell is configured to acquire magnetic field information between a corresponding pair of adjacent electrodes.

9. The image generation apparatus according to claim 1, wherein each sensor cell is configured to acquire magnetic field information from a corresponding pair of opposing electrodes.

10. The image generation apparatus according to claim 1, wherein each sensor cell is configured to acquire magnetic field information from an arbitrarily chosen pair of electrodes.

11. A method for generating a tomographic image of a measurement object, the method comprising:
preparing a base member on which a plurality of electrodes and a plurality of sensor cells are provided;
inputting an alternating current of a high frequency more than 100 kHz and equal to or less than 10 MHz to the measurement object via the plurality of electrodes on the base member while the plurality of electrodes on the base member do not contact a body surface of the measurement object, the alternating current flowing from a first electrode of the plurality of electrodes to a second electrode of the plurality of electrodes without attaching the electrodes to the body surface of the measurement object;
acquiring an intensity of a magnetic field generated by the alternating current via the plurality of sensor cells; and
moving the base member relative to the measurement object in a predetermined direction while the plurality of electrodes and the plurality of sensor cells on the base member do not contact the body surface of the measurement object,
wherein moving the base member relative to the measurement object in the predetermined direction also moves the electrodes and the sensor cells relative to the measurement object in the predetermined direction, and
wherein before reaching the measurement object, the alternating current travels through a volume of air that intervenes between the electrodes and the measurement object.

12. A method for generating a tomographic image of a measurement object, the method comprising:
preparing a base member on which a plurality of electrodes and a magnetic sensor are provided;
inputting an alternating current of a high frequency more than 100 kHz and equal to or less than 10 MHz to the measurement object via the plurality of electrodes on the base member while the plurality of electrodes on the base member do not contact a body surface of the measurement object, the alternating current flowing from a first electrode of the plurality of electrodes to a second electrode of the plurality of electrodes without being attached to the body surface of the measurement object;
acquiring an intensity of a magnetic field generated by the alternating current via the magnetic sensor; and
moving the base member relative to the measurement object in a predetermined direction while the plurality of electrodes on the base member is in non-direct contact with the body surface of the measurement object,
wherein moving the base member relative to the measurement object in the predetermined direction also moves the electrodes and the magnetic sensor relative to the measurement object in the predetermined direction, and
wherein before reaching the measurement object, the alternating current travels through a volume of air that intervenes between the electrodes and the measurement object.

13. An image generation apparatus comprising:
a plurality of electrodes;
a magnetic sensor;
a base member on which the plurality of electrodes and the magnetic sensor are provided;
an input device configured to input an alternating current of a high frequency more than 100 kHz and equal to or less than 10 MHz to a measurement object via the plurality of electrodes; and
a controller configured to provide a tomographic image of a measurement object based on an intensity of a magnetic field generated by the alternating current, the controller being further configured to acquire the intensity of the magnetic field via the magnetic sensor,
wherein the base member is configured to maintain an air gap between the electrodes and the measurement object in use so that the alternating current travels through a volume of air before reaching the measurement object,
wherein the plurality of electrodes are configured so that the alternating current flows from a first electrode of the plurality of electrodes to a second electrode of the plurality of electrodes without attaching the first and second electrodes to a body surface of the measurement object, and
wherein the base member, the electrodes, and the magnetic sensor are movable together relative to the measurement object in a predetermined direction.

14. A non-transitory computer-readable storage medium that stores a program that allows a computer to execute the function of the image generation apparatus according to claim 13 so that the computer executes the steps comprising:
a program for causing an image generation apparatus to function as:
inputting the alternating current of a high frequency more than 100 kHz and equal to or less than 10 MHz to the measurement object via the plurality of electrodes on the base member while the plurality of electrodes on the base member is in non-direct contact with a body surface of the measurement object to cause an alternating current to flow between two electrodes among the plurality of electrodes without directly attaching the electrodes to the body surface of the measurement object; and
moving the base member relative to the measurement object in a predetermined direction while the plurality of electrodes on the base member is in non-direct contact with the body surface of the measurement object, wherein moving the base member relative to the measurement object in the predetermined direction also moves the electrodes relative to the measurement object in the predetermined direction, and wherein before reaching the measurement object, the alternating current travels through a volume of air that intervenes between the electrodes and the measurement object.

15. The image generation apparatus according to claim 14, wherein the controller acquires at least intensities of magnetic fields at a plurality of positions surrounding a specific tomographic surface of the measurement object.

16. The image generation apparatus according to claim 14, wherein the input device inputs the alternating current via electrodes arranged at a plurality of positions surrounding a specific tomographic surface of the measurement object.

17. The image generation apparatus according to claim 14, wherein the controller acquires an intensity of a magnetic field generated based on an alternating current input by the input device via the magnetic sensor arranged around the same tomographic surface as a specific tomographic surface of the measurement object.

18. The image generation apparatus according to claim 14, wherein the electrodes are made of a non-magnetic material.

19. The image generation apparatus according to claim 14, wherein the magnetic sensor is an optical pumping atomic magnetic sensor.

20. An image generation apparatus comprising:
two electrodes;
one sensor cell;
a base member on which the two electrodes and the one sensor cell are provided;
an input device configured to input an alternating current of a high frequency more than 100 kHz and equal to or less than 10 MHz to a measurement object via the two electrodes, the two electrodes being separated from the measurement object; and
a controller configured to provide a tomographic image of a measurement object based on an intensity of a magnetic field generated by the alternating current, the controller being further configured to acquire the intensity of the magnetic field via the one sensor cell,
wherein the base member is configured to maintain an air gap between the electrodes and the measurement object in use so that the alternating current travels through a volume of air before reaching the measurement object,
wherein the two electrodes are configured so that the alternating current flowing from a first one of the two electrodes to a second one of the two electrodes without attaching the electrodes to a body surface of the measurement object, and
wherein the base member, the electrodes, and the sensor cell are movable together relative to the measurement object in a predetermined direction.

21. The image generation apparatus according to claim 20, wherein the one sensor cell is arranged between the two electrodes.

22. The image generation apparatus according to claim 20, wherein the base member has a cylindrical shape.

\* \* \* \* \*